(12) United States Patent
Katz et al.

(10) Patent No.: US 11,407,649 B2
(45) Date of Patent: Aug. 9, 2022

(54) CERIUM (III) CARBONATE FORMULATIONS

(71) Applicant: The Regents of the University of California, Berkeley, CA (US)

(72) Inventors: Alexander Katz, Berkeley, CA (US); Manish Mishra, Berkeley, CA (US)

(73) Assignee: The Regents of the University of California, Berkeley, CA (US)

( * ) Notice: Subject to any disclaimer, the term of this patent is extended or adjusted under 35 U.S.C. 154(b) by 0 days.

(21) Appl. No.: 16/856,178

(22) Filed: Apr. 23, 2020

(65) Prior Publication Data

US 2020/0339435 A1    Oct. 29, 2020

Related U.S. Application Data

(60) Provisional application No. 62/837,657, filed on Apr. 23, 2019.

(51) Int. Cl.
| | | |
|---|---|---|
| *C01F 17/247* | (2020.01) | |
| *C09B 31/057* | (2006.01) | |
| *C09B 21/00* | (2006.01) | |
| *C09C 1/10* | (2006.01) | |
| *C09C 1/20* | (2006.01) | |
| *C09C 1/24* | (2006.01) | |
| *C09C 1/34* | (2006.01) | |
| *C09C 1/42* | (2006.01) | |
| *C09C 1/48* | (2006.01) | |
| *C09C 1/00* | (2006.01) | |
| *C09C 1/02* | (2006.01) | |
| *C09C 1/04* | (2006.01) | |
| *C09C 1/36* | (2006.01) | |
| *C01G 23/04* | (2006.01) | |

(52) U.S. Cl.
CPC ............ *C01F 17/247* (2020.01); *C01G 23/04* (2013.01); *C09B 21/00* (2013.01); *C09B 31/057* (2013.01)

(58) Field of Classification Search
None
See application file for complete search history.

(56) References Cited

U.S. PATENT DOCUMENTS

2012/0107604 A1*  5/2012  Aruga ................... C09D 7/68
                                                            428/328

OTHER PUBLICATIONS

Molla et al., "Facile synthesis and structural analysis of graphene oxide decorated with iron-cerium carbonate for visible-light driven rapid degradation of organic dyes." Journal of Environmental Chemical Engineering, vol. 6 (2018), pp. 2616-2626. Available online as of Apr. 6, 2018.*
Xu et al., "Template-free synthesis of mesoporous $CeO_2$ powders by integrating bottom-up and top-down routes for acid orange 7 adsorption." RSC Adv. (2015), 5, 44828-44834 (published May 12, 2015).*
Liu et al., "Precipitation and characterization of cerous carbonate," J. Cryst. Growth, 1999, 206:88-92.
Zhai et al., "Preparation, characterization and photocatalytic activity of $CeO_2$ nanocrystalline using ammonium bicarbonate as precipitant," Mater. Lett., 2007, 61:1863-1866.

(Continued)

*Primary Examiner* — Daniel Berns
(74) *Attorney, Agent, or Firm* — Riverside Law LLP

(57) ABSTRACT

The disclosure provides, inter alia, formulations comprising cerium (III) carbonate, and processes for producing cerium (III) carbonate. In embodiments, the disclosure provides methods for passivating photodegradation of organic compounds using cerium (III) carbonate.

15 Claims, 16 Drawing Sheets

(56) References Cited

OTHER PUBLICATIONS

Adachi et al., "The Binary Rare Earth Oxides," Chem. Rev. 1998, 98:1479-1514.
Baldim et al., "The enzyme-like catalytic activity of cerium oxide nanoparticles and its dependency on Ce3+ surface area concentration," Nanoscale, 2018, 10:6971-6980.
Montini et al., "Fundamentals and Catalytic Applications of CeO2-Based Materials," Chem. Rev., 2016, 116:5987-6041.
Zhu, "Functional ceria-salt-composite materials for advanced ITSOFC applications," Journal of Power Sources, 2003, 114:1-9.
Wang et al., "Ceria-based nanocomposite with simultaneious proton and oxygen ion conductivity for low-temperature solid oxide fuel cells," Journal of Power Sources, 2011, 196:2754-2758.
Ferreira et al., "Intrinsic and extrinsic compositional effects in ceria/carbonate composite electrolytes for fuel cells," International Journal of Hydrogen Energy, 2011, 36:3704-3711.
Jain et al., "Role of salt phase in GDC and alumina-based composites," Ionics, 2010, 16:487-496.
Benamira et al., "Gadolinia-doped ceria mixed with alkali carbonates for solid oxide fuel cell applications: I. A thermal, structural and morphological insight," Journal of Power Sources, 2011, 196:5546-5554.
Wang et al. "Novel core-shell SDC/amorphous Na2CO3 nanocomposite electrolyte for low-temperature SOFCs," Electrochemistry Communications, 2008, 10:1617-1620.
Li et al., "Effective ionic conductivity of a novel intermediate-temperature mixed oxide-ion and carbonate-ion conductor," J. Electrochem. Soc., 2011, 158:B225-B232.

\* cited by examiner

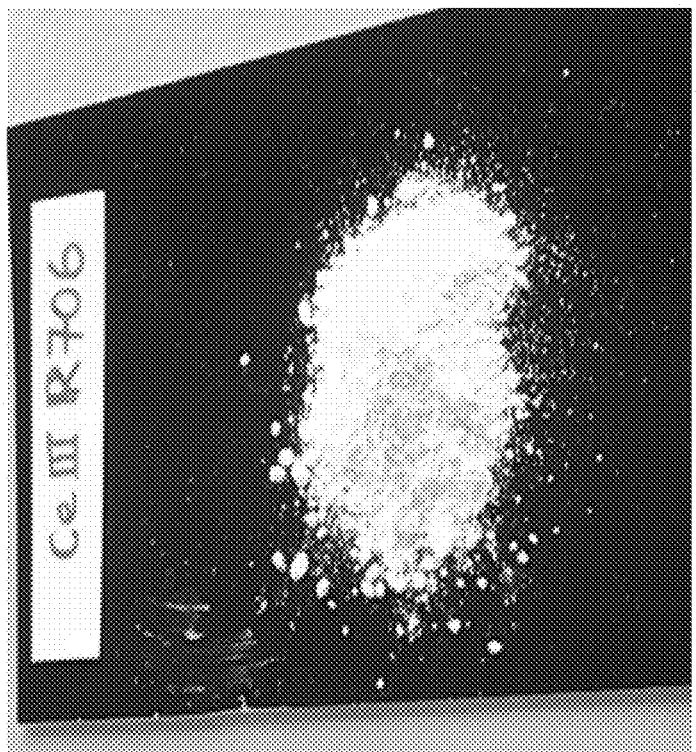
FIG. 4A
FIG. 4B

US 11,407,649 B2

CERIUM (III) CARBONATE FORMULATIONS

CROSS-REFERENCE TO RELATED APPLICATIONS

This application claims priority to U.S. Provisional Patent Application Ser. No. 62/837,657, filed Apr. 23, 2019, the entire content of which is incorporated herein by reference.

BACKGROUND

Organic compounds are susceptible to photodegradation, and some compounds, such as pigments (e.g., $TiO_2$), are well-known photocatalysts. Photocatalytic activity initiated and promoted by the pigment is rooted in the generation of reactive oxygen species (ROS), which are known to cause degradation of organic compounds. In order to reduce the photocatalytic activity, the pigments are therefore generally modified with a thin overcoating (~5-10 nm) of metal oxides such as $SiO_2$, $Al_2O_3$, $ZrO_2$, or mixtures thereof. These metal oxides promote a decrease in the photocatalytic activity of the pigment and/or synthesis of ROS such as hydroxyl radicals (OH), superoxide radical anion $O_2^-$, and hydrogen peroxide $H_2O_2$, all of which photodegrade and oxidatively decompose organic compounds.

There is a need in the art to inhibit photodegradation of organic compounds. The disclosure is directed to this, as well as other, important ends.

BRIEF SUMMARY

The disclosure provides cerium (III) carbonate of the formula $Ce_2(CO_3)_3 \cdot xH_2O$, wherein x is zero or a positive number; and wherein the cerium (III) carbonate releases at least 27.6 wt % $CO_2$ when normalized to the dry weight of the cerium (III) carbonate, during thermogravimetric analysis. In aspects, the cerium (III) carbonate is substantially free of cerium (IV) and/or is substantially free of a cerium-oxide phase.

The disclosure provides formulations comprising cerium (III) carbonate and an organic compound susceptible to photodegradation. In embodiments, the disclosure provides formulations comprising cerium (III) carbonate, an organic compound susceptible to photodegradation, and a photocatalytically active pigment. In embodiments, the disclosure provides formulations comprising cerium (III) carbonate, an organic compound susceptible to photodegradation, a photocatalytically active pigment, and water.

The disclosure provides processes for producing cerium (III) carbonate by (i) mixing a carbonate salt and water to form a first solution; (ii) mixing a cerium (III) salt and water to form a second solution; (iii) mixing the first solution and the second solution to form a third solution, wherein the third solution has a pH of 9.2 or less; and (iv) centrifuging the third solution to form the cerium (III) carbonate. In aspects, the carbonate salt is ammonium carbonate, and the cerium (III) salt is ammonium cerium (III) nitrate tetrahydrate. In aspects, the cerium (III) carbonate is $Ce_2(CO_3)_3 \cdot 4H_2O$. In aspects, the third solution has a pH from about 9.0 to 9.2. Alternatively, the disclosure provides a process for producing cerium (III) carbonate by (i) mixing two solids comprising a carbonate salt and a cerium (III) salt (in the absence of added water); (ii) washing away any excess salts with water and centrifuging the resulting mixture to provide the solid cerium (III) carbonate.

The disclosure provides processes for producing the formulations by mixing a cerium (III) carbonate source material with an organic compound susceptible to photodegradation.

These and other embodiments are described herein.

BRIEF DESCRIPTION OF THE DRAWINGS

FIG. 2A is a photograph showing unchanged color of pure $SiO_2$ powder after Ce(III) precipitation on $SiO_2$ and FIG. 2B is a plot of methylene blue (MB) dye (10 mL of $10^{-5}$ M) photodegradation (under 254 nm light) with 50 mg of P25 in presence of 5 mg Ce(III)-$SiO_2$ in the surface area ratio of 1:0.877.

FIG. 3A is a photograph showing rutile $TiO_2$ powder before (left sample) and after Ce(III) precipitation (right sample) on its surface, and FIG. 3B is a plot of kinetics of $10^{-5}$ M MB organic dye degradation with 2 mg of P25 and in the presence of 5.7 mg Ce(III)-$TiO_2$ under 254 nm light.

FIGS. 4A-4B are photographs showing no colour difference between unmodified Ti-Pure R706 (FIG. 4A) and Ce(III)-R706 (FIG. 4B).

Figure 13A:
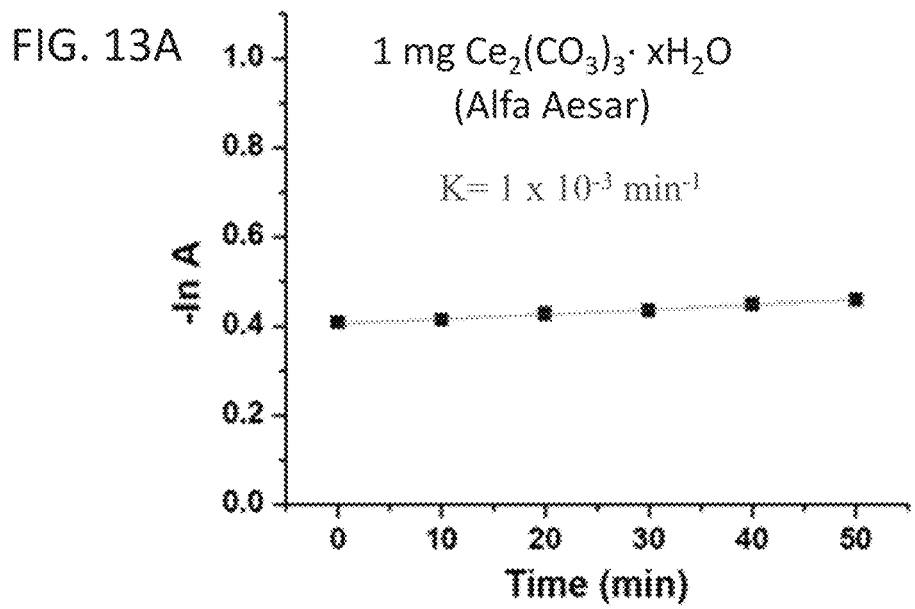
FIGS. 13A-13C are plots of kinetics of $10^{-5}$ M MB organic dye degradation (under 254 nm light) in presence of 2 mg of P25, 11.4 mg of unmodified R706 and separately added: (i) 1 mg of $Ce_2(CO_3)_3 \cdot xH_2O$ (Alfa Aesar) (FIG.
Figure 13B:
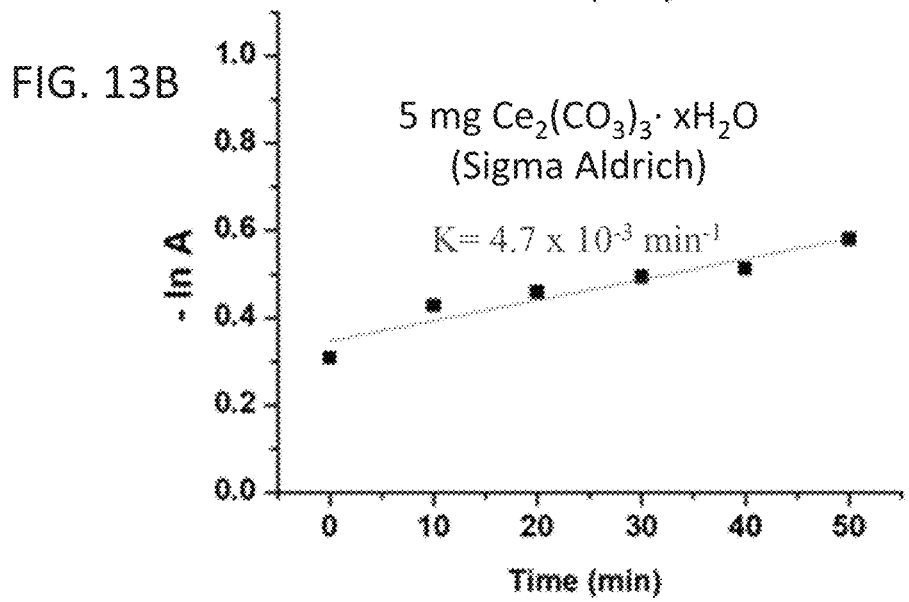
Figure 13C:
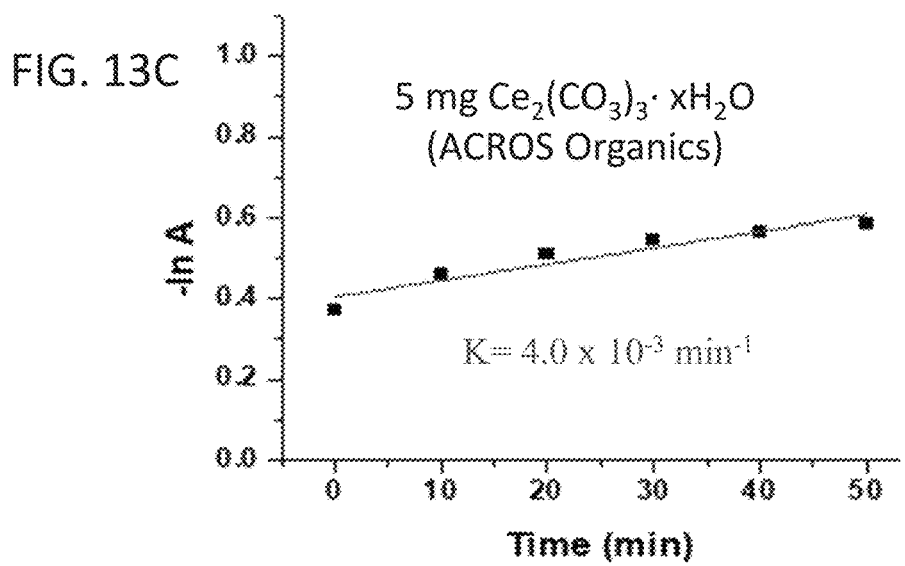

13A); (ii) 5 mg $Ce_2(CO_3)_3 \cdot xH_2O$ (Sigma Aldrich) (FIG. 13B); (iii) 5 mg of $Ce_2(CO_3)_3 \cdot xH_2O$ (ACROS Organics) (FIG. 13C).

Figure 14:
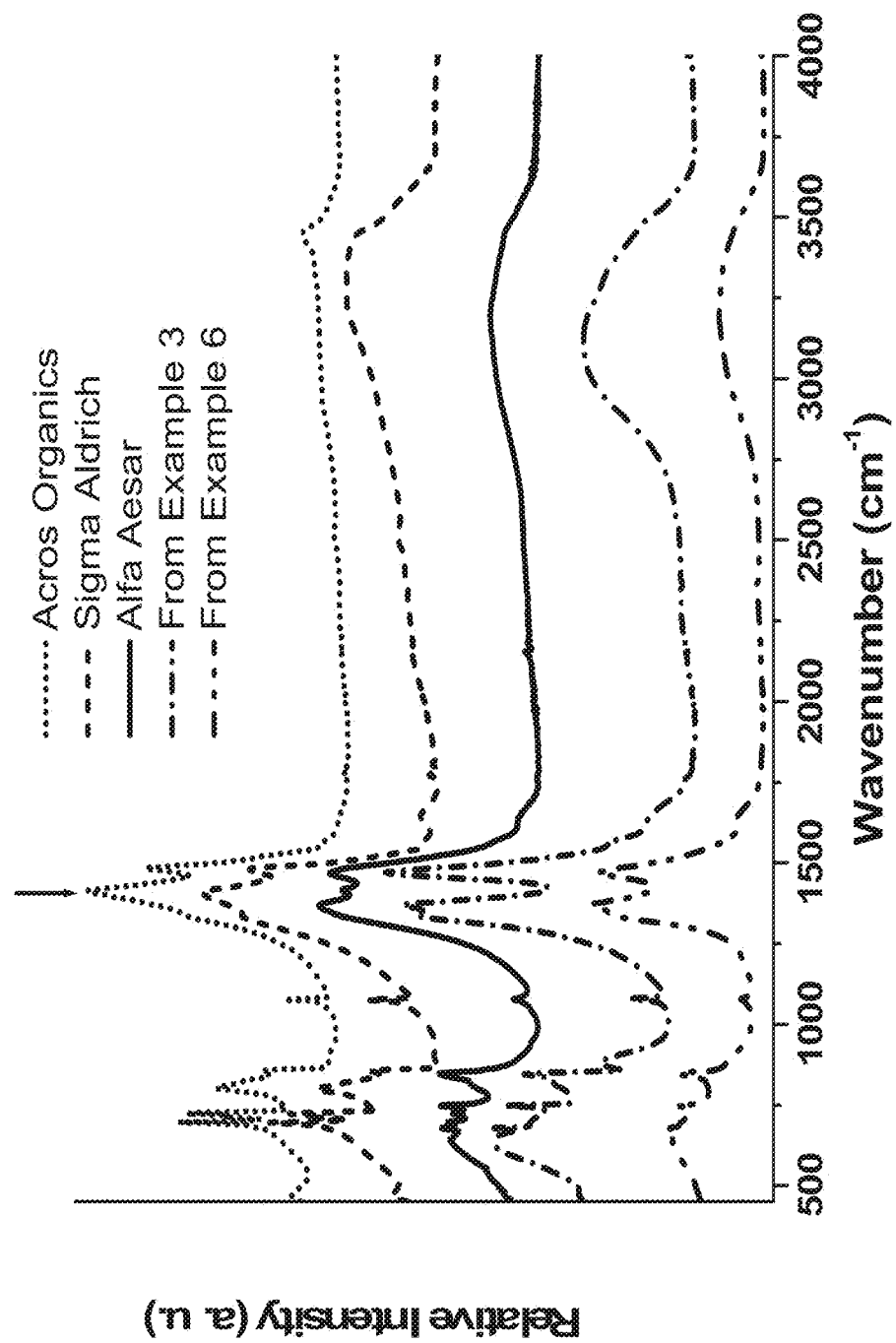

FIG. 14 provides ATR-FTIR spectra of different cerium (III) carbonate materials comprising those synthesized in Examples 3 and 6 (samples were dried under ambient conditions for 48 hours prior to analysis), as well as commercially available samples from Sigma Aldrich, Acros Organics, and Alfa Aesar. The vertical arrow represents the frequency of the 1410 $cm^{-1}$ band that represents weakly electrostatically attached carbonate, and is draw at the top as a guide to the eye.

Figure 15A:
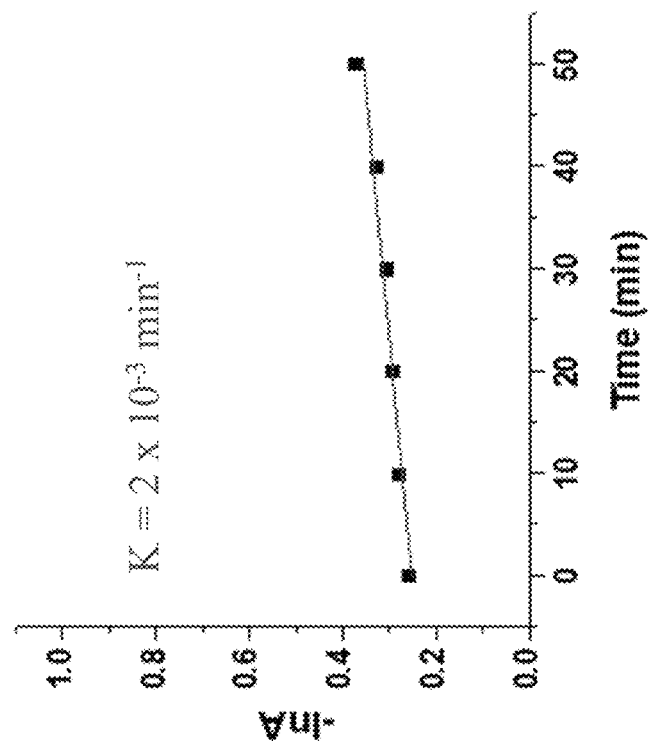
Figure 15B:
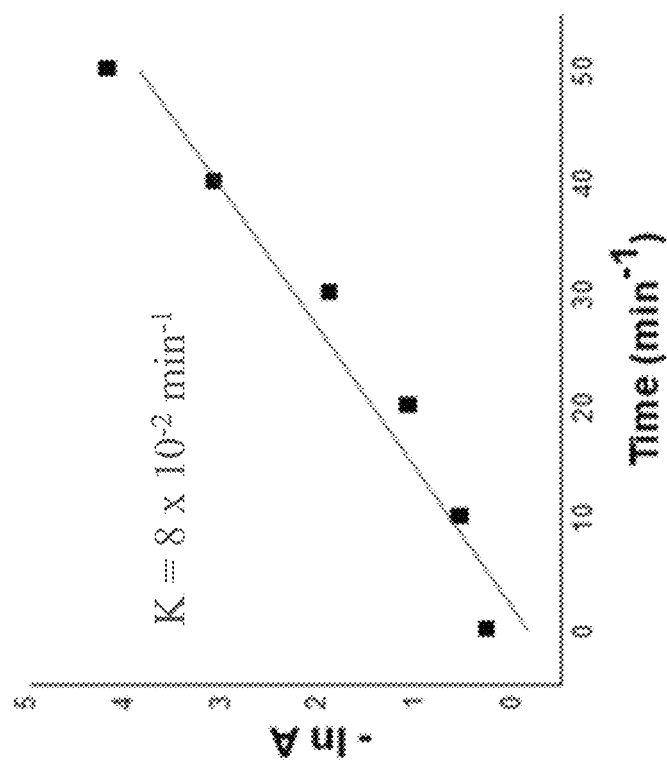

FIGS. 15A-15B. FIG. 15A provides photodegradation kinetics data for 10 mL aqueous solution of $10^{-5}$ M MB dye that was exposed to 254 nm light under a photoreactor setup for a duration of up to 60 minutes. FIG. 15B provides photodegradation kinetics data for 10 mL aqueous solution of $10^{-5}$ M MB dye and 1 mg $Ce_2(CO_3)_3 \cdot 4H_2O$ (synthesized by the procedure described in Example 3) that was exposed to 254 nm light under a photoreactor setup for a duration of up to 60 minutes.

Figure 16:
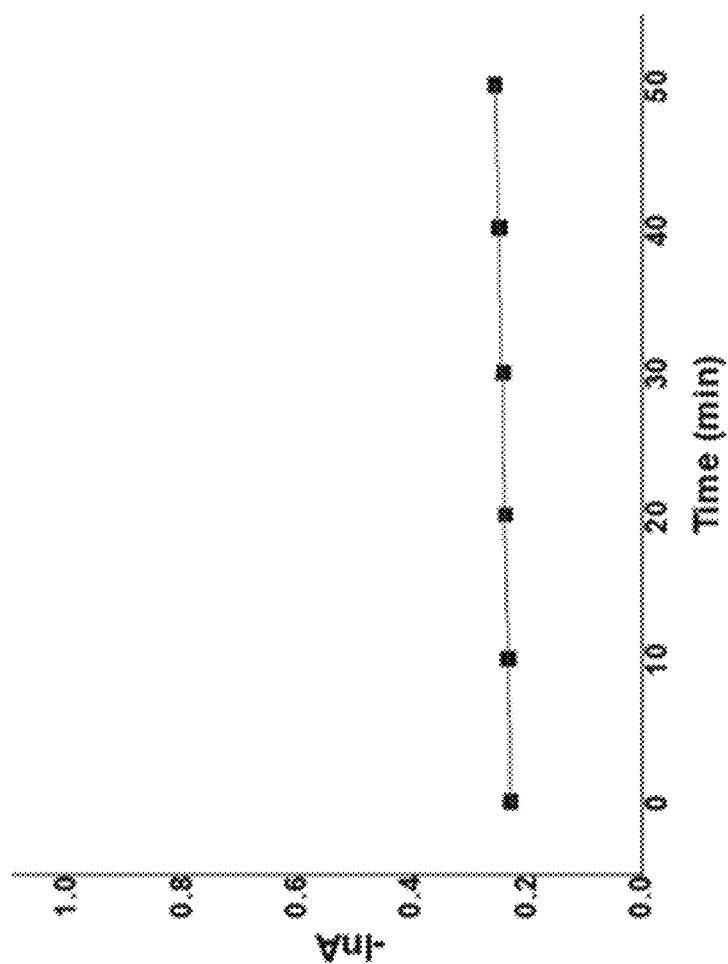

FIG. 16 is a plot of the kinetics of $10^{-5}$ M MB organic dye degradation (under 254 nm light) in presence of 2 mg of P25, 11.4 mg of unmodified R706 and separate phase of 1 mg of $Ce_2(CO_3)_3 \cdot 4H_2O$.

DETAILED DESCRIPTION

Definitions

"Cerium (III) carbonate" refers to a material that comprises $Ce_2(CO_3)_3$. In aspects, the cerium (III) carbonate is substantially free of cerium (IV) and/or a cerium-oxide phase. In aspects, the $Ce_2(CO_3)_3$ is white in appearance. In aspects, cerium (III) carbonate is substantially free of cerium (IV) if it is white in appearance and does not have a yellowish tint. In aspects, the $Ce_2(CO_3)_3$ is $Ce_2(CO_3)_3 \cdot xH_2O$ where x is either zero or a positive number. In aspects, the positive number is an integer from 1 to 6. In aspects, the $Ce_2(CO_3)_3 \cdot xH_2O$ is $Ce_2(CO_3)_3 \cdot 4H_2O$. In aspects, thermogravimetric analysis is used to determine if cerium (III) carbonate is substantially free of a cerium-oxide phase, because such a cerium (III) carbonate releases a higher wt % $CO_2$ when normalized to the dry weight of the cerium (III) carbonate, during thermogravimetric analysis, compared with a cerium (III) carbonate that also contains a cerium-oxide phase. The quantity of $CO_2$ released upon heating a sample of cerium (III) carbonate is measured via thermogravimetric analysis as described below. In aspects, the cerium (III) carbonate releases at least 21.9 wt % $CO_2$ when normalized to the dry weight of the cerium (III) carbonate, during thermogravimetric analysis. In aspects, the cerium (III) carbonate releases at least 27 wt % $CO_2$ when normalized to the dry weight of the cerium (III) carbonate, during thermogravimetric analysis. In aspects, the cerium (III) carbonate releases at least 27.5 wt % $CO_2$ when normalized to the dry weight of the cerium (III) carbonate, during thermogravimetric analysis. In aspects, the cerium (III) carbonate releases at least 27.6 wt % $CO_2$ when normalized to the dry weight of the cerium (III) carbonate, during thermogravimetric analysis. In aspects, the cerium (III) carbonate releases at least 28.0 wt % $CO_2$ when normalized to the dry weight of the cerium (III) carbonate, during thermogravimetric analysis. In aspects, the cerium (III) carbonate releases at least 28.5 wt % $CO_2$ when normalized to the dry weight of the cerium (III) carbonate, during thermogravimetric analysis. In aspects, the cerium (III) carbonate releases at least 29.0 wt % $CO_2$ when normalized to the dry weight of the cerium (III) carbonate, during thermogravimetric analysis. In aspects, cerium (III) carbonate comprises at least 5.7 wt % carbon and at least 0.9 wt % hydrogen as measured by CHN analysis. In aspects, cerium (III) carbonate comprises at least 6.5 wt % carbon and at least 1.45 wt % hydrogen as measured by CHN analysis. In aspects, cerium (III) carbonate comprises about 6.7 wt % carbon and about 1.76 wt % hydrogen as measured by CHN analysis. In aspects, cerium (III) carbonate has a ratio of a peak intensity at 1410 $cm^{-1}$ to a peak intensity at 1468 $cm^{-1}$ of about 1.3 or less, as measured by ATR-FTIR. In aspects, cerium (III) carbonate has a ratio of a peak intensity at 1410 $cm^{-1}$ to a peak intensity at 1468 $cm^{-1}$ of about 0.9 or less, as measured by ATR-FTIR. In aspects, cerium (III) carbonate has a ratio of a peak intensity at 1410 $cm^{-1}$ to a peak intensity at 1468 $cm^{-1}$ of about 0, as measured by ATR-FTIR. In aspects, cerium (III) carbonate is substantially insoluble in water.

"Cerium (III) carbonate source material" refers to cerium (III) carbonate obtained from a commercial supplier or manufactured by methods known in the art or manufactured by the methods described herein. In aspects, the cerium (III) carbonate source material is substantially free of cerium (IV) and/or a cerium-oxide phase. In aspects, the cerium (III) carbonate source material is white in appearance. In aspects, the cerium (III) carbonate source material is substantially free of cerium (IV) if it is white in appearance and does not have a yellowish tint. In aspects, a cerium (III) carbonate source material releases at least 21.9 wt % $CO_2$ when normalized to the dry weight of the cerium (III) carbonate source material, during thermogravimetric analysis. In aspects, a cerium (III) carbonate source material releases at least 27 wt % $CO_2$ when normalized to the dry weight of the cerium (III) carbonate source material, during thermogravimetric analysis. In aspects, a cerium (III) carbonate source material releases at least 27.5 wt % $CO_2$ when normalized to the dry weight of the cerium (III) carbonate source material, during thermogravimetric analysis. In aspects, the cerium (III) carbonate source material releases at least 27.6 wt % $CO_2$ when normalized to the dry weight of the cerium (III) carbonate source material, during thermogravimetric analysis. In aspects, the cerium (III) carbonate source material releases at least 28.0 wt % $CO_2$ when normalized to the dry weight of the cerium (III) carbonate source material, during thermogravimetric analysis. In aspects, the cerium (III) carbonate source material releases at least 28.5 wt % $CO_2$ when normalized to the dry weight of the cerium (III) carbonate source material, during thermogravimetric analysis. In aspects, a cerium (III) carbonate source material releases at least 29.0 wt % $CO_2$ when normalized to the dry weight of the cerium (III) carbonate source material, during thermogravimetric analysis. In aspects, a cerium (III) carbonate source material comprises at least 5.7 wt % carbon and at least 0.9 wt % hydrogen as measured by CHN analysis. In aspects, a cerium (III) carbonate source material comprises at least 6.5 wt % carbon and at least 1.45 wt % hydrogen as measured by CHN analysis. In aspects, a cerium (III) carbonate source material comprises about 6.7 wt % carbon and about 1.76 wt % hydrogen as measured by CHN analysis. In aspects, the cerium (III) carbonate source material has a ratio of a peak intensity at 1410 $cm^{-1}$ to a peak intensity at 1468 $cm^{-1}$ of about 1.3 or less, as measured by ATR-FTIR. In aspects, the cerium (III) carbonate source material has a ratio of a peak intensity at 1410 $cm^{-1}$ to a peak intensity at 1468 $cm^{-1}$ of about 1 or less, as measured by ATR-FTIR. In aspects, the cerium (III) carbonate source material has a ratio of a peak intensity at 1410 $cm^{-1}$ to a peak intensity at 1468 cm$^{-1}$ of about 0.9 or less, as measured by ATR-FTIR. In aspects, the cerium (III) carbonate source material has a ratio of a peak intensity at 1410 cm$^{-1}$ to a peak intensity at 1468 cm$^{-1}$ of about 0, as measured by ATR-FTIR. In aspects, a cerium (III) carbonate source material is $Ce_2(CO_3)_3 \cdot xH_2O$, where x is 0 or a positive integer. In aspects, x is 0, 1, 2, 3, 4, 5, or 6. In aspects, a cerium (III) carbonate source material is $Ce_2(CO_3)_3 \cdot 4H_2O$. In aspects, a cerium (III) carbonate source material is substantially insoluble in water.

"Thermogravimetric analysis" refers to the analytical technique that relies on weighing a sample of cerium carbonate during its heating in dry air at a ramp rate of 5° C./min, during which the sample thermally decomposes to synthesize cerium oxide and $CO_2$ in the temperature range of 200° C. to 575° C. For the purposes of this specification, the amount of $CO_2$ released is calculated by subtracting the weight of the sample at 200° C. from the weight at 575° C., and this weight difference is divided by the weight of the sample at 200° C., to give the weight fraction of $CO_2$ released normalized to the dry weight of cerium carbonate. The trends in the quantity of $CO_2$ released from cerium carbonate as measured via thermogravimetric analysis in this fashion generally agree with trends of the carbon content of cerium carbonate as measured by CHN analysis, between different samples. Thermogravimetric analysis is further described by Liu et al, J. Cryst. Growth, 206:88-92 (1999) and Zhai et al, Mater. Lett., 61:1863-1866 (2007).

"CHN analysis" refers to the analysis of the amount of carbon (C), hydrogen (H), and nitrogen (N) in a compound or composition. CHN analysis can be performed by scientific equipment known in the art, such as a 2400 CHN Elemental Analyzer by Perkin Elmer, a CE440 Elemental Analyser by Exeter Analytical, and the like. CHN analysis is well-known in the art.

"Attenuated total reflectance Fourier transform infrared spectroscopy" and "ATR-FTIR" refer to the spectroscopic technique that measures the changes that occur in an internally reflected infrared beam when the beam comes into contact with a sample. ATR-FTIR is well-known in the art and described for example, in Technical Note, "FT-IR Spectroscopy, Attenuated Total Reflectance (ATR) by Perkin Elmer (2005).

"White" refers to compounds and compositions that are white in appearance and/or that are a mixture of all of the wavelengths of the visible spectrum, e.g., light wavelengths of about 380 nm to about 750 nm. In aspects, the term "white in appearance" includes all shades of white, such as pure white, alabaster, cream, eggshell, ivory, Navajo white, vanilla, and the like. In aspects, the term "white in appearance" includes all shades of white that do not visually have a yellowish tint to them. In aspects, the term "white in appearance" is brilliant white, which has an absence of absorbance in the yellow-color region of the visible spectrum (e.g., absence of absorbance at wavelengths from about 565 nm to about 590 nm), as ascertained by solid-state UV-Visible spectroscopy (such measurements are known to one in the prior art and can be made for example with the use of a diffuse-reflectance accessory, see J. Am. Chem. Soc. 2004, 126, 16478-16486).

"Substantially insoluble in water" refers to a compound (e.g., cerium (III) carbonate) that has a solubility of less than 1 wt % in water. In aspects, the compound (e.g., cerium (III) carbonate) that has a solubility of less than 0.5 wt % in water. In aspects, the compound (e.g., cerium (III) carbonate) that has a solubility of less than 0.25 wt % in water. In aspects, the compound (e.g., cerium (III) carbonate) that has a solubility of less than 0.1 wt % in water.

"Cerium (III) carbonate average particle size" refers to the radius of gyration and is measured by electron microscopy. The cerium (III) carbonate can be any particle size in the formulations described herein. In aspects, the cerium (III) carbonate average particle size is from about 1 nanometer to about 100 microns. In aspects, the cerium (III) carbonate average particle size is from about 10 nanometers to about 10 microns. In aspects, the cerium (III) carbonate average particle size is from about 10 nanometers to about 1 micron. In aspects, the cerium (III) carbonate average particle size is from about 30 nanometers to about 500 nanometers. In aspects, the cerium (III) carbonate average particle size is from about 40 nanometers to about 300 nanometers. In aspects, the cerium (III) carbonate average particle size is from about 1 nanometer to about 80 nanometers. In aspects, the cerium (III) carbonate average particle size is from about 1 nanometer to about 50 nanometers. In aspects, the cerium (III) carbonate average particle size is from about 1 nanometer to about 80 nanometers. In aspects, the cerium (III) carbonate average particle size is from about 1 nanometer to about 40 nanometers.

"Photocatalytically active pigment" refers to a pigment that accelerates the rate of photodegradation of organic compounds. A photocatalytically active pigment is capable of catalyzing some chemical reactions when irradiated with light of a suitable wavelength. For example, in the presence of light and/or air and/or water, the surface of a photocatalytically active pigment can synthesize highly potent oxidants, which lead to the transformation and/or decomposition of organic substances. Such organic substances are referred to herein as organic compounds susceptible to photodegradation. In aspects, the photocatalytically active pigment is a metal oxide, a metal sulfide, or a combination thereof. In aspects, the photocatalytically active pigment is a metal oxide. In aspects, the photocatalytically active pigment is titanium dioxide, zinc oxide, cerium oxide, zirconium oxide, tungsten oxide, vanadium oxide, tin oxide, nickel oxide, copper oxide, molybdenum oxide, tungsten sulfide, cadmium sulfide, cadmium selenide, zinc sulfide, or a combination of two or more thereof. In aspects, the photocatalytically active pigment is titanium dioxide. In aspects, the highly potent oxidants are ROS.

"Same phase" refers to the cerium (III) carbonate being precipitated in the presence of an existing surface of a different phase, e.g., inorganic-oxide particle surface, such as a photocatalytically active pigment (e.g., $TiO_2$). In aspects of the "same phase," the cerium (III) carbonate at least partially coats an inorganic oxide particle surface, such as a photocatalytically active pigment (e.g., $TiO_2$). In aspects of the "same phase," the cerium (III) carbonate is ionically or covalently bonded to an inorganic oxide particle surface, such as a photocatalytically active pigment (e.g., $TiO_2$).

"Separate phase" refers the cerium (III) carbonate not being precipitated proximate to any existing surface of a different phase (e.g., inorganic-oxide particle surface or a photocatalytically active pigment), but rather precipitated to form its own phase of cerium (III) carbonate that is independent of their proximity to a pigment or photocatalytic particle, which by virtue of its insolubility in water, remains as its own distinct particle, within an aqueous dispersion.

"Substantially free of cerium (IV)" refers to formulations or compositions that are substantially free of cerium (IV). In aspects, the formulations comprise less than 50 wt % cerium (IV). In aspects, the formulations comprises less than 10 wt % cerium (IV). In aspects, the formulations comprises less than 1.0 wt % cerium (IV). In aspects, the formulations comprises less than 0.5 wt % cerium (IV). In aspects, the formulations comprise no detectable amount of cerium (IV).

"Cerium oxide" or "cerium oxide phase" refer to cerium oxide as defined below. In aspects, cerium oxide includes substances represented by the chemical formula $CeO_y$, where y is 1.5 to 2. The cerium oxide has a coloration by appearance of yellowish-white when y is 2 and golden yellow when y is 1.5. Whereas $CeO_2$ crystallizes in the fluorite structure, for sub-stoichiometric oxides comprising 1.5<y<2, there is typically a mixture of Ce(III) and Ce(IV), as well as oxygen vacancies in the structure. In aspects, "cerium oxide" includes hydrated oxide structures as represented by the chemical formula $CeO_y \cdot aH_2O$, where a is typically a number below 10 and y is 1.5 to 2. In aspects "cerium oxide" includes cerium oxyhydroxide, which has a chemical formula $Ce(O)_x(OH)_z$ where (x+2z)=1.5 to 2. Cerium oxides that are oxyhydroxides can also be hydrated, with typical molar ratios of Ce to $H_2O$ being less than 10 in these structures. Many phases of cerium oxides have been identified, and some of these phases can be represented in a $Ce_2O_3$—$CeO_2$ phase diagram (see Chem. Rev. 1998, 98, 1479-1514). Some known phases of cerium oxide include but are not limited to cubic cerium oxide, cubic ceria, cubic cerianite, triclinic cerium oxide, rhombohedral cerium oxide, and triclinic cerium oxide. Generally, the relative quantity of sub-stoichiometric oxide and Ce(III) increases as the nanoparticle size of the cerium oxide decreases; for 4.5 nm cerium-oxide nanoparticles, a Ce(III) to Ce(IV) ratio approaching 0.75 has been reported (see Nanoscale 2018, 10, 6971-6980) via X-ray photoelectron spectroscopy. It is generally known that cerium oxides form mixtures with carbonates (see cited references 305-311 of Chem. Rev. 2016, 116, 5987-6041 for examples), and in the present disclosure, it is undesired to have a cerium-oxide phase present as a mixture within the cerium-carbonate material. Examples of such mixtures, which for the purposes of this disclosure are also cerium oxides, include but are not limited to cerium oxide carbonate hydrate, hydroxylbastnasite, cerium carbonate hydroxide hydrate, cerium oxalate carbonate hydrate, cerium aqua carbonate oxalate hydrate and orthorhombic cerium carbonate hydroxide. While characterization of $CeO_2$ can be performed by powder X-ray diffraction, this method is known in the art to be less sensitive to the presence and detection of sub-stoichiometric oxides of ceria (see pp. of 5989-5990 of Chem. Rev. 2016, 116, 5987-6041 for a discussion of this). Nevertheless, the skilled artisan would understand that powder X-ray diffraction data for various cerium oxide structures is publicly available from the International Center for Diffraction Data (ICDD). Some of these structures correspond to ICDD codes (01-072-6357), (01-075-7751), (01-075-7749), (01-075-8371), (01-071-4807), (01-075-9470), (01-075-5980), (01-073-9516), (01- 073-6328), (01-071-4199), (01-089-8429), (01-089-8430), (01-075-7752), (03-065-2975), (01-089-8436), (01-081-0792), (03-065-5923), (01-075-7750), (01-089-8435), (01-089-8431), (01-073-6318), (01-075-7754), (01-071-0567), (01-089-8432), (01-075-7755), (01-075-7758), (01-075-7753), (01-075-7757), (01-075-7756), (01-089-8434), (00-046-0369), (00-032-0189), (00-028-0897), (01-089-2794), (00-051-0549), (00-43-0602), (00-44-0617), and (00-041-0013). The skilled artisan would know it is possible to test a cerium carbonate material for lack of a cerium oxide phase by powder X-ray diffraction, by ensuring that the powder X-ray pattern for this material lacks peaks corresponding to one or more of the cerium-oxide structures listed above, among other cerium-oxide structures that are not listed. However, as mentioned above, this method lacks sensitivity for certain cerium-oxides such as sub-stoichiometric cerium oxides, and amorphous cerium oxides. For the purposes of this disclosure, the methods for assessing the absence of a cerium oxide phase in a cerium carbonate sample are a coloration of white by appearance (i.e., lacking of a yellowish tint) as well as a large mass % of $CO_2$ release as assessed by thermogravimetric analysis of the cerium carbonate.

"Substantially free of cerium oxide" or "substantially free of a cerium oxide phase" refers to formulations or compositions that are substantially free of a cerium oxide phase. In aspects, the formulations comprise less than 50 wt % of cerium oxide. In aspects, the formulations comprises less than 10 wt % cerium oxide. In aspects, the formulations comprises less than 5 wt % cerium oxide. In aspects, the formulations comprises less than 2 wt % cerium oxide. In aspects, the formulations comprises less than 1.0 wt % cerium oxide. In aspects, the formulations comprises less than 0.5 wt % cerium oxide. In aspects, the formulations comprises less than 0.1 wt % cerium oxide. In aspects, the formulations comprise no detectable amount of cerium oxide.

"Organic compound susceptible to photodegradation" refers to an organic compound that undergoes photodegradation over a period of time. In aspects, an organic compound susceptible to photodegradation has a measurable decrease in concentration after exposure to light when compared to the same organic compound that is not exposed to light (i.e., is left in the dark). The light can be UV light, visible light, or a combination thereof.

"Titanium dioxide" or "$TiO_2$" can be in any form. In aspects, the $TiO_2$ comprises brookite type, rutile type, anataste type, or a combination of two or more thereof. In aspects, the $TiO_2$ comprises rutile type and anataste type. In aspects, the $TiO_2$ is rutile type. In aspects, the $TiO_2$ is anataste type. In aspects, the weight % of rutile type to anataste type in the $TiO_2$ is from about 70:30 to about 95:5. In aspects, the weight % of rutile type to anataste type in the $TiO_2$ is from about 75:25 to about 95:5. In aspects, the weight % of rutile type to anataste type in the $TiO_2$ is from about 80:20 to about 90:10. In aspects, the weight % of rutile type to anataste type in the $TiO_2$ is about 85:15.

"P25" refers to $TiO_2$ comprising 85 wt % rutile type $TiO_2$ and 15 wt % anataste type $TiO_2$.

"R706" refers to a Ti-Pure R706 material, which is known in the art to comprise a rutile $TiO_2$ core of 290 nm in diameter and an aluminosilicate shell that serves as an overcoat of this core, which has a thickness of ~5-10 nm. One of the functions of this overcoat is to decrease the photocatalytic activity of the R706 pigment. A person familiar with the art of the invention would understand that R706 is a standard commercially available pigment commonly used in paints and coatings.

"Mixing time" pertains to a situation when a certain volume of a first solution is added to a second solution. The mixing time is the time that it takes to add the entire volume of the first solution to the second solution, when forming a mixture of the two solutions.

"Directly" refers to the delay when adding a freshly prepared first mixture in a synthesis to another solid or mixture. In this context, "directly" means immediately after the synthesis of the first mixture, with a typical delay of less than 1 minute, or 40 seconds, or 30 seconds after synthesis of the first mixture, this first mixture was added to another solid or mixture.

The terms "composition" and "formulation" are used interchangeably for the purposes of this disclosure.

Cerium (III) Carbonate

The disclosure provides cerium (III) carbonate of the formula $Ce_2(CO_3)_3 \cdot xH_2O$ wherein x is zero or a positive number. In aspects, x is 0, 1, 2, 3, 4, 5, or 6. In aspects, x is 0. In aspects, x is 1, In aspects, x is 2. In aspects, x is 3. In aspects, x is 4. In aspects, x is 5. In aspects, x is 6. In aspects, the cerium (III) carbonate is substantially free of cerium (IV). In aspects, the cerium (III) carbonate is substantially free of a cerium-oxide phase. In aspects, the cerium (III) carbonate is substantially free of cerium (IV) and is substantially free of a cerium-oxide phase. In aspects, the cerium (III) carbonate releases at least 27.6 wt % $CO_2$ when normalized to the dry weight of the cerium (III) carbonate, during thermogravimetric analysis. In aspects, x is 6. In aspects, the cerium (III) carbonate is white in appearance. In aspects, thermogravimetric analysis is used to determine if cerium (III) carbonate is substantially free of a cerium-oxide phase, because such a cerium (III) carbonate releases a higher wt % $CO_2$ when normalized to the dry weight of the cerium (III) carbonate, during thermogravimetric analysis, compared with a cerium (III) carbonate that also contains a cerium-oxide phase. The quantity of $CO_2$ released upon heating a sample of cerium (III) carbonate is measured via thermogravimetric analysis. In aspects, the cerium (III) carbonate releases at least 27.7 wt % $CO_2$ when normalized to the dry weight of the cerium (III) carbonate, during thermogravimetric analysis. In aspects, the cerium (III) carbonate releases at least 27.8 wt % $CO_2$ when normalized to the dry weight of the cerium (III) carbonate, during thermogravimetric analysis. In aspects, the cerium (III) carbonate releases at least 27.9 wt % $CO_2$ when normalized to the dry weight of the cerium (III) carbonate, during thermogravimetric analysis. In aspects, the cerium carbonate releases at least 28 wt % $CO_2$ when normalized to the dry weight of the cerium (III) carbonate, during thermogravimetric analysis. In aspects, the cerium (III) carbonate releases at least 28.5 wt % $CO_2$ when normalized to the dry weight of the cerium (III) carbonate, during thermogravimetric analysis. In aspects, the cerium (III) carbonate releases at least 28.6 wt % $CO_2$ when normalized to the dry weight of the cerium (III) carbonate, during thermogravimetric analysis. In aspects, the cerium (III) carbonate releases at least 28.7 wt % $CO_2$ when normalized to the dry weight of the cerium (III) carbonate, during thermogravimetric analysis. In aspects, the cerium (III) carbonate releases at least 28.8 wt % $CO_2$ when normalized to the dry weight of the cerium (III) carbonate, during thermogravimetric analysis. In aspects, the cerium (III) carbonate releases at least 28.9 wt % $CO_2$ when normalized to the dry weight of the cerium (III) carbonate, during thermogravimetric analysis. In aspects, the cerium (III) carbonate releases at least 29 wt % $CO_2$ when normalized to the dry weight of the cerium (III) carbonate, during thermogravimetric analysis. In aspects, cerium (III) carbonate has a ratio of a peak intensity at 1410 $cm^{-1}$ to a peak intensity at 1468 $cm^{-1}$ of about 1.2 or less, as measured by ATR-FTIR. In aspects, cerium (III) carbonate has a ratio of a peak intensity at 1410 $cm^{-1}$ to a peak intensity at 1468 $cm^{-1}$ of about 1.1 or less, as measured by ATR-FTIR. In aspects, cerium (III) carbonate has a ratio of a peak intensity at 1410 $cm^{-1}$ to a peak intensity at 1468 $cm^{-1}$ of about 1.0 or less, as measured by ATR-FTIR. In aspects, cerium (III) carbonate has a ratio of a peak intensity at 1410 $cm^{-1}$ to a peak intensity at 1468 $cm^{-1}$ of about 0.95 or less, as measured by ATR-FTIR. In aspects, cerium (III) carbonate has a ratio of a peak intensity at 1410 $cm^{-1}$ to a peak intensity at 1468 $cm^{-1}$ of about 0.9 or less, as measured by ATR-FTIR. In aspects, cerium (III) carbonate comprises at least 6.6 wt % carbon and at least 1.5 wt % hydrogen as measured by CHN analysis. In aspects, cerium (III) carbonate comprises at least 6.6 wt % carbon and at least 1.6 wt % hydrogen as measured by CHN analysis. In aspects, cerium (III) carbonate comprises at least 6.6 wt % carbon and at least 1.7 wt % hydrogen as measured by CHN analysis. In aspects, cerium (III) carbonate comprises at least 6.7 wt % carbon and at least 1.7 wt % hydrogen as measured by CHN analysis. In aspects, cerium (III) carbonate comprises about 6.7 wt % carbon and about 1.76 wt % hydrogen as measured by CHN analysis. In aspects, the disclosure provides the cerium (III) carbonate described herein and an organic compound susceptible to photodegradation. In aspects, the disclosure provides methods of inhibiting photodegradation of an organic compound by mixing the cerium (III) carbonate described herein with an organic compound susceptible to photodegradation, thereby inhibiting photodegradation of the organic compound.

Formulations: Cerium (III) Carbonate and Organic Compound

The disclosure provides formulations comprising cerium (III) carbonate and an organic compound susceptible to photodegradation. In aspects, the cerium (III) carbonate source material is $Ce_2(CO_3)_3 \cdot xH_2O$ where x is either zero or a positive number. In aspects, the positive number is an integer from 1 to 6. In aspects, the cerium carbonate source material is $Ce_2(CO_3)_3 \cdot 4H_2O$. In aspects, the cerium (III) carbonate source material is substantially free of cerium (IV) and/or is substantially free of a cerium-oxide phase. In embodiments, the cerium (III) carbonate is obtained from a cerium (III) carbonate source material releases at least 21.9 wt % $CO_2$ when normalized to the dry weight of the cerium (III) carbonate source material, during thermogravimetric analysis. In embodiments, the cerium (III) carbonate is obtained from a cerium (III) carbonate source material releases at least 27.5 wt % $CO_2$ when normalized to the dry weight of the cerium (III) carbonate source material, during thermogravimetric analysis. In embodiments, the cerium (III) carbonate is obtained from a cerium (III) carbonate source material releases at least 27.6 wt % $CO_2$ when normalized to the dry weight of the cerium (III) carbonate source material, during thermogravimetric analysis. In aspects, the cerium (III) carbonate source material releases at least 28.0 wt % $CO_2$ when normalized to the dry weight of the cerium (III) carbonate source material, during thermogravimetric analysis. In aspects, the cerium (III) carbonate source material releases at least 28.5 wt % $CO_2$ when normalized to the dry weight of the cerium (III) carbonate source material, during thermogravimetric analysis. In embodiments, the cerium (III) carbonate is obtained from a cerium (III) carbonate source material releases at least 29.0 wt % $CO_2$ when normalized to the dry weight of the cerium (III) carbonate source material, during thermogravimetric analysis. In embodiments, the cerium (III) carbonate is obtained from a cerium (III) carbonate source material comprising at least 5.7 wt % carbon and at least 0.9 wt % hydrogen as measured by CHN analysis. In embodiments, the cerium (III) carbonate is obtained from a cerium (III) carbonate source material comprising at least 6.5 wt % carbon and at least 1.45 wt % hydrogen as measured by CHN analysis. In embodiments, the cerium (III) carbonate is obtained from a cerium (III) carbonate source material comprising about 6.7 wt % carbon and about 1.76 wt % hydrogen as measured by CHN analysis. In embodiments, the cerium (III) carbonate source material has an intensity of about 1.3 or less at the bands ranging from 1410 cm$^{-1}$ to 1468 cm$^{-1}$ as measured by ATR-FTIR. In embodiments, the cerium (III) carbonate source material has an intensity of about 1.0 or less at the bands ranging from 1410 cm$^{-1}$ to 1468 cm$^{-1}$ as measured by ATR-FTIR. In embodiments, the cerium (III) carbonate source material has an intensity of about 0.9 or less at the bands ranging from 1410 cm$^{-1}$ to 1468 cm$^{-1}$ as measured by ATR-FTIR. In embodiments, the cerium (III) carbonate source material has an intensity of about 0 at the bands ranging from 1410 cm$^{-1}$ to 1468 cm$^{-1}$ as measured by ATR-FTIR. In embodiments, the cerium (III) carbonate source material is white. In embodiments, the cerium (III) carbonate source material is substantially insoluble in water.

In the formulations described herein, cerium (III) carbonate is present in an amount of about 0.05 wt % to about 20 wt % based on the total weight of the formulation. In the formulations described herein, cerium (III) carbonate is present in an amount of about 0.1 wt % to about 15 wt % based on the total weight of the formulation. In the formulations described herein, cerium (III) carbonate is present in an amount of about 1 wt % to about 10 wt % based on the total weight of the formulation. In the formulations described herein, cerium (III) carbonate is present in an amount of about 1 wt % to about 5 wt % based on the total weight of the formulation.

In the formulations described herein, the organic compound susceptible to photodegradation is present in an amount from about 1 wt % to about 75 wt % of the total weight of the formulation. In aspects, the organic compound susceptible to photodegradation is present in an amount from about 1 wt % to about 50 wt % of the total weight of the formulation. In aspects, the organic compound susceptible to photodegradation is present in an amount from about 1 wt % to about 40 wt % of the total weight of the formulation. In aspects, the organic compound susceptible to photodegradation is present in an amount from about 3 wt % to about 35 wt % of the total weight of the formulation. In aspects, the organic compound susceptible to photodegradation is present in an amount from about 5 wt % to about 30 wt % of the total weight of the formulation.

In the formulations described herein, the cerium compound has a molar cerium (III) to cerium (IV) ratio of greater than 1, as measured by X-ray photoelectron spectroscopy (XPS), and to this end most preferably comprises ligands that stabilize the cerium in the (III) rather than (IV) oxidation state. Such ligands are known in the art of the invention to comprise phosphate and carbonate ligands.

The disclosure provides formulations comprising cerium (III) carbonate and an organic compound susceptible to photodegradation. In aspects, the cerium (III) carbonate is $Ce_2(CO_3)_3 \cdot xH_2O$ where x is either zero or a positive number. In aspects, the positive number is an integer from 1 to 6. In aspects, the cerium (III) carbonate is $Ce_2(CO_3)_3 \cdot 4H_2O$. In aspects, the cerium (III) carbonate source material is substantially free of cerium (IV) and/or is substantially free of a cerium-oxide phase. In embodiments, the cerium (III) carbonate releases at least 21.9 wt % $CO_2$ when normalized to the dry weight of the cerium (III) carbonate, during thermogravimetric analysis. In embodiments, the cerium (III) carbonate releases at least 27.5 wt % $CO_2$ when normalized to the dry weight of the cerium (III) carbonate, during thermogravimetric analysis. In embodiments, the cerium (III) carbonate releases at least 27.6 wt % $CO_2$ when normalized to the dry weight of the cerium (III) carbonate, during thermogravimetric analysis. In aspects, the cerium (III) carbonate releases at least 28.0 wt % $CO_2$ when normalized to the dry weight of the cerium (III) carbonate, during thermogravimetric analysis. In aspects, the cerium (III) carbonate releases at least 28.5 wt % $CO_2$ when normalized to the dry weight of the cerium (III) carbonate, during thermogravimetric analysis. In embodiments, the cerium (III) carbonate releases at least 29.0 wt % $CO_2$ when normalized to the dry weight of the cerium (III) carbonate, during thermogravimetric analysis. In embodiments, the cerium (III) carbonate comprises at least 5.7 wt % carbon and at least 0.9 wt % hydrogen as measured by CHN analysis. In embodiments, the cerium (III) carbonate comprises at least 6.5 wt % carbon and at least 1.45 wt % hydrogen as measured by CHN analysis. In embodiments, the cerium (III) carbonate comprises about 6.7 wt % carbon and about 1.76 wt % hydrogen as measured by CHN analysis. In embodiments, the cerium (III) carbonate has an intensity of about 1.3 or less at the bands ranging from 1410 cm$^{-1}$ to 1468 cm$^{-1}$ as measured by ATR-FTIR. In embodiments, the cerium (III) carbonate has an intensity of about 1.0 or less at the bands ranging from 1410 cm$^{-1}$ to 1468 cm$^{-1}$ as measured by ATR-FTIR. In embodiments, the cerium (III) carbonate has an intensity of about 0.9 or less at the bands ranging from 1410 cm$^{-1}$ to 1468 cm$^{-1}$ as measured by ATR-FTIR. In embodiments, the cerium (III) carbonate has an intensity of about 0 at the bands ranging from 1410 cm$^{-1}$ to 1468 cm$^{-1}$ as measured by ATR-FTIR. In embodiments, the cerium (III) carbonate is white. In embodiments, the cerium (III) carbonate is substantially insoluble in water.

In the formulations described herein, cerium (III) carbonate is present in an amount of about 0.005 wt % to about 20 wt % based on the total weight of the formulation. In the formulations described herein, cerium (III) carbonate is present in an amount of about 0.01 wt % to about 15 wt % based on the total weight of the formulation. In the formulations described herein, cerium (III) carbonate is present in an amount of about 0.1 wt % to about 10 wt % based on the total weight of the formulation. In the formulations described herein, cerium (III) carbonate is present in an amount of about 0.1 wt % to about 5 wt % based on the total weight of the formulation.

In the formulations described herein, the organic compound susceptible to photodegradation is present in an amount from about 1 wt % to about 75 wt % of the total weight of the formulation. In aspects, the organic compound susceptible to photodegradation is present in an amount from about 1 wt % to about 50 wt % of the total weight of the formulation. In aspects, the organic compound susceptible to photodegradation is present in an amount from about 1 wt % to about 40 wt % of the total weight of the formulation. In aspects, the organic compound susceptible to photodegradation is present in an amount from about 3 wt % to about 35 wt % of the total weight of the formulation. In aspects, the organic compound susceptible to photodegradation is present in an amount from about 5 wt % to about 30 wt % of the total weight of the formulation.

In the formulations described herein, the cerium compound has a molar cerium (III) to cerium (IV) ratio of greater than 1, as measured by X-ray photoelectron spectroscopy (XPS), and to this end most preferably comprises ligands that stabilize the cerium in the (III) rather than (IV) oxidation state. Such ligands are known in the art of the invention to comprise phosphate and carbonate ligands.

Formulations: Cerium (III) Carbonate, Organic Compound, Photocatalytically Active Pigment The disclosure provides formulations comprising cerium (III) carbonate, an organic compound susceptible to photodegradation, and a photocatalytically active pigment. In aspects, the formulation optionally further comprise a solvent, such as water. In aspects, the formulation optionally further comprises one or more dyes. In aspects, the cerium (III) carbonate source materials is $Ce_2(CO_3)_3 \cdot xH_2O$ where x is either zero or a positive number. In aspects, the positive number is an integer from 1 to 6. In aspects, the cerium (III) carbonate source material is $Ce_2(CO_3)_3 \cdot 4H_2O$. In aspects, the cerium (III) carbonate source material is substantially free of cerium (IV) and/or is substantially free of a cerium-oxide phase. In embodiments, the cerium (III) carbonate is obtained from a cerium (III) carbonate source material that releases at least 21.9 wt % $CO_2$ when normalized to the dry weight of the cerium (III) carbonate source material, during thermogravimetric analysis. In embodiments, the cerium (III) carbonate is obtained from a cerium (III) carbonate source material that releases at least 27.5 wt % $CO_2$ when normalized to the dry weight of the cerium (III) carbonate source material, during thermogravimetric analysis. In embodiments, the cerium (III) carbonate is obtained from a cerium (III) carbonate source material that releases at least 27.6 wt % $CO_2$ when normalized to the dry weight of the cerium (III) carbonate source material, during thermogravimetric analysis. In aspects, the cerium (III) carbonate source material releases at least 28.0 wt % $CO_2$ when normalized to the dry weight of the cerium (III) carbonate source material, during thermogravimetric analysis. In aspects, the cerium (III) carbonate source material releases at least 28.5 wt % $CO_2$ when normalized to the dry weight of the cerium (III) carbonate source material, during thermogravimetric analysis. In embodiments, the cerium (III) carbonate is obtained from a cerium (III) carbonate source material that releases at least 29.0 wt % $CO_2$ when normalized to the dry weight of the cerium (III) carbonate source material, during thermogravimetric analysis. In embodiments, the cerium (III) carbonate is obtained from a cerium (III) carbonate source material comprising at least 5.7 wt % carbon and at least 0.9 wt % hydrogen as measured by CHN analysis. In embodiments, the cerium (III) carbonate is obtained from a cerium (III) carbonate source material comprising at least 6.5 wt % carbon and at least 1.45 wt % hydrogen as measured by CHN analysis. In embodiments, the cerium (III) carbonate is obtained from a cerium (III) carbonate source material comprising about 6.7 wt % carbon and about 1.76 wt % hydrogen as measured by CHN analysis. In embodiments, the cerium (III) carbonate source material has an intensity of about 1.3 or less at the bands ranging from 1410 $cm^{-1}$ to 1468 $cm^{-1}$ as measured by ATR-FTIR. In embodiments, the cerium (III) carbonate source material has an intensity of about 1.0 or less at the bands ranging from 1410 $cm^{-1}$ to 1468 $cm^{-1}$ as measured by ATR-FTIR. In embodiments, the cerium (III) carbonate source material has an intensity of about 0.9 or less at the bands ranging from 1410 $cm^{-1}$ to 1468 $cm^{-1}$ as measured by ATR-FTIR. In embodiments, the cerium (III) carbonate source material has an intensity of about 0 at the bands ranging from 1410 $cm^{-1}$ to 1468 $cm^{-1}$ as measured by ATR-FTIR. In embodiments, the cerium (III) carbonate source material is white. In embodiments, the cerium (III) carbonate source material is substantially insoluble in water. In embodiments, photocatalytically active pigment comprises titanium dioxide.

In the formulations described herein, cerium (III) carbonate is present in an amount of about 0.005 wt % to about 20 wt % based on the total weight of the formulation. In the formulations described herein, cerium (III) carbonate is present in an amount of about 0.01 wt % to about 15 wt % based on the total weight of the formulation. In the formulations described herein, cerium (III) carbonate is present in an amount of about 0.1 wt % to about 10 wt % based on the total weight of the formulation. In the formulations described herein, cerium (III) carbonate is present in an amount of about 0.1 wt % to about 5 wt % based on the total weight of the formulation.

In embodiments, cerium (III) carbonate is present in an amount of about 0.5 wt % to about 20 wt % relative to the weight of the photocatalytically active pigment. In the formulations described herein, cerium (III) carbonate is present in an amount of about 1 wt % to about 15 wt % relative to the weight of the photocatalytically active pigment. In the formulations described herein, cerium (III) carbonate is present in an amount of about 1 wt % to about 10 wt % relative to the weight of the photocatalytically active pigment. In the formulations described herein, cerium (III) carbonate is present in an amount of about 1 wt % to about 5 wt % relative to the weight of the photocatalytically active pigment. In the formulations described herein, cerium (III) carbonate is present in an amount of about 1 wt % to about 4 wt % relative to the weight of the photocatalytically active pigment. In the formulations described herein, cerium (III) carbonate is present in an amount of about 1 wt % to about 3 wt % relative to the weight of the photocatalytically active pigment. In the formulations described herein, cerium (III) carbonate is present in an amount of about 2 wt % relative to the weight of the photocatalytically active pigment.

In the formulations described herein, the organic compound susceptible to photodegradation is present in an amount from about 1 wt % to about 75 wt % of the total weight of the formulation. In aspects, the organic compound susceptible to photodegradation is present in an amount from about 1 wt % to about 50 wt % of the total weight of the formulation. In aspects, the organic compound susceptible to photodegradation is present in an amount from about 1 wt % to about 40 wt % of the total weight of the formulation. In aspects, the organic compound susceptible to photodegradation is present in an amount from about 3 wt % to about 35 wt % of the total weight of the formulation. In aspects, the organic compound susceptible to photodegradation is present in an amount from about 5 wt % to about 30 wt % of the total weight of the formulation.

The formulations may optionally comprise water. In the formulations described herein, water is present in an amount from about 1 wt % to about 70 wt % of the total weight of the formulation. In aspects, water is present in an amount from about 1 wt % to about 65 wt % of the total weight of the formulation. In aspects, water is present in an amount from about 5 wt % to about 60 wt % of the total weight of the formulation. In aspects, water is present in an amount from about 10 wt % to about 60 wt % of the total weight of the formulation.

The formulations may optionally comprise one or more dyes. In the formulations described herein, dyes are optionally present in the formulation in an amount from about 0.1 wt % to about 50 wt % of the total weight of the formulation. In aspects, dyes are present in the formulation in an amount from about 0.1 wt % to about 40 wt % of the total weight of the formulation. In aspects, dyes are present in the formulation in an amount from about 1 wt % to about 35 wt % of the total weight of the formulation. In aspects, dyes are present in the formulation in an amount from about 5 wt % to about 30 wt % of the total weight of the formulation.

In the formulations described herein, the cerium compound has a molar cerium (III) to cerium (IV) ratio of greater than 1, as measured by X-ray photoelectron spectroscopy (XPS), and to this end most preferably comprises ligands that stabilize the cerium in the (III) rather than (IV) oxidation state.

In embodiments, the cerium (III) carbonate is in the same phase as the photocatalytically active pigment. In aspects, the cerium (III) carbonate is precipitated in the presence of the photocatalytically active pigment and/or is in close proximity to the photocatalytically active pigment. In other words, the cerium (III) carbonate particles are associated with or are in intimate mechanical contact with the photocatalytically active pigment particle. In aspects, the cerium (III) carbonate contacts the photocatalytically active pigment surface. In aspects, the cerium (III) carbonate is deposited or precipitated in the presence of the photocatalytically active pigment. In aspects, the cerium compound undergoes macroscale precipitation upon the photocatalytically active pigment.

In embodiments, the cerium (III) carbonate is in a separate phase from the photocatalytically active pigment. In embodiments, the cerium (III) carbonate is not precipitated upon the photocatalytically active pigment and/or is not in close proximity to the photocatalytically active pigment. In other words, the cerium (III) carbonate particles should not associate with or be in intimate mechanical contact with the photocatalytically active pigment particle. In embodiments, the cerium (III) carbonate does not contact the photocatalytically active pigment surface. In embodiments, the cerium (III) carbonate is not deposited or precipitated upon the photocatalytically active pigment. In embodiments, the cerium compound does not undergo macroscopic phase separation and remains uniformly dispersed in the formulation (which is a fluid) or in a composition that may be either wet or dry).

The disclosure provides formulations comprising cerium (III) carbonate, an organic compound susceptible to photodegradation, and a photocatalytically active pigment. In aspects, the formulation optionally further comprises a solvent, such as water. In aspects, the formulation optionally further comprises one or more dyes. In aspects, the cerium (III) carbonate is $Ce_2(CO_3)_3 \cdot xH_2O$ where x is either zero or a positive number. In aspects, the positive number is an integer from 1 to 6. In aspects, the cerium (III) carbonate source material is substantially free of cerium (IV) and/or is substantially free of a cerium-oxide phase. In aspects, the cerium (III) carbonate is $Ce_2(CO_3)_3 \cdot 4H_2O$. In embodiments, the cerium (III) carbonate releases at least 21.9 wt % $CO_2$ when normalized to the dry weight of the cerium (III) carbonate source material, during thermogravimetric analysis. In embodiments, the cerium (III) carbonate releases at least 27.5 wt % $CO_2$ when normalized to the dry weight of the cerium (III) carbonate source material, during thermogravimetric analysis. In embodiments, the cerium (III) carbonate releases at least 27.6 wt % $CO_2$ when normalized to the dry weight of the cerium (III) carbonate source material, during thermogravimetric analysis. In aspects, the cerium (III) carbonate releases at least 28.0 wt % $CO_2$ when normalized to the dry weight of the cerium (III) carbonate, during thermogravimetric analysis. In aspects, the cerium (III) carbonate releases at least 28.5 wt % $CO_2$ when normalized to the dry weight of the cerium (III) carbonate, during thermogravimetric analysis. In embodiments, the cerium (III) carbonate releases at least 29.0 wt % $CO_2$ when normalized to the dry weight of the cerium (III) carbonate source material, during thermogravimetric analysis. In embodiments, the cerium (III) carbonate comprises at least 5.7 wt % carbon and at least 0.9 wt % hydrogen as measured by CHN analysis. In embodiments, the cerium (III) carbonate comprises at least 6.5 wt % carbon and at least 1.45 wt % hydrogen as measured by CHN analysis. In embodiments, the cerium (III) carbonate comprises about 6.7 wt % carbon and about 1.76 wt % hydrogen as measured by CHN analysis. In embodiments, the cerium (III) carbonate has an intensity of about 1.3 or less at the bands ranging from 1410 $cm^{-1}$ to 1468 $cm^{-1}$ as measured by ATR-FTIR. In embodiments, the cerium (III) carbonate has an intensity of about 1.0 or less at the bands ranging from 1410 $cm^{-1}$ to 1468 $cm^{-1}$ as measured by ATR-FTIR. In embodiments, the cerium (III) carbonate has an intensity of about 0.9 or less at the bands ranging from 1410 $cm^{-1}$ to 1468 $cm^{-1}$ as measured by ATR-FTIR. In embodiments, the cerium (III) carbonate has an intensity of about 0 at the bands ranging from 1410 $cm^{-1}$ to 1468 $cm^{-1}$ as measured by ATR-FTIR. In embodiments, the cerium (III) carbonate is white. In embodiments, the cerium (III) carbonate is substantially insoluble in water. In embodiments, photocatalytically active pigment comprises titanium dioxide.

In the formulations described herein, cerium (III) carbonate is present in an amount of about 0.005 wt % to about 20 wt % based on the total weight of the formulation. In the formulations described herein, cerium (III) carbonate is present in an amount of about 0.01 wt % to about 15 wt % based on the total weight of the formulation. In the formulations described herein, cerium (III) carbonate is present in an amount of about 0.1 wt % to about 10 wt % based on the total weight of the formulation. In the formulations described herein, cerium (III) carbonate is present in an amount of about 0.1 wt % to about 5 wt % based on the total weight of the formulation.

In embodiments, cerium (III) carbonate is present in an amount of about 0.5 wt % to about 20 wt % relative to the weight of the photocatalytically active pigment. In the formulations described herein, cerium (III) carbonate is present in an amount of about 1 wt % to about 15 wt % relative to the weight of the photocatalytically active pigment. In the formulations described herein, cerium (III) carbonate is present in an amount of about 1 wt % to about 10 wt % relative to the weight of the photocatalytically active pigment. In the formulations described herein, cerium (III) carbonate is present in an amount of about 1 wt % to about 5 wt % relative to the weight of the photocatalytically active pigment. In the formulations described herein, cerium (III) carbonate is present in an amount of about 1 wt % to about 4 wt % relative to the weight of the photocatalytically active pigment. In the formulations described herein, cerium (III) carbonate is present in an amount of about 1 wt % to about 3 wt % relative to the weight of the photocatalytically active pigment. In the formulations described herein, cerium (III) carbonate is present in an amount of about 2 wt % relative to the weight of the photocatalytically active pigment.

In the formulations described herein, the organic compound susceptible to photodegradation is present in an amount from about 1 wt % to about 75 wt % of the total weight of the formulation. In aspects, the organic compound susceptible to photodegradation is present in an amount from about 1 wt % to about 50 wt % of the total weight of the formulation. In aspects, the organic compound susceptible to photodegradation is present in an amount from about 1 wt % to about 40 wt % of the total weight of the formulation. In aspects, the organic compound susceptible to photodegradation is present in an amount from about 3 wt % to about 35 wt % of the total weight of the formulation. In aspects, the organic compound susceptible to photodegradation is present in an amount from about 5 wt % to about 30 wt % of the total weight of the formulation.

In the formulations described herein, the cerium compound has a molar cerium (III) to cerium (IV) ratio of greater than 1, as measured by X-ray photoelectron spectroscopy (XPS), and to this end most preferably comprises ligands that stabilize the cerium in the (III) rather than (IV) oxidation state.

In embodiments, the cerium (III) carbonate is in the same phase as the photocatalytically active pigment. In embodiments, the cerium (III) carbonate is precipitated in the presence of the photocatalytically active pigment and/or is in close proximity to the photocatalytically active pigment. In other words, the cerium (III) carbonate particles are associated with or form coordinate compounds with the photocatalytically active pigment. In embodiments, the cerium (III) carbonate contacts the photocatalytically active pigment. In embodiments, the cerium (III) carbonate is deposited or precipitated in the presence of the photocatalytically active pigment. In embodiments, the cerium compound undergoes macroscale precipitation upon the photocatalytically active pigment.

In embodiments, the cerium (III) carbonate is in a separate phase from the photocatalytically active pigment. In embodiments, the cerium (III) carbonate is not precipitated upon the photocatalytically active pigment and/or is no in close proximity to the photocatalytically active pigment. In other words, the cerium (III) carbonate particles should not associate with or be in intimate mechanical contact with the photocatalytically active pigment particle. In embodiments, the cerium (III) carbonate does not contact the photocatalytically active pigment surface. In embodiments, the cerium (III) carbonate is not deposited or precipitated upon the photocatalytically active pigment. In embodiments, the cerium compound does not undergo macroscopic phase separation and remains uniformly dispersed in the formulation (which is a fluid) or in a composition that may be either wet or dry).

Formulations: Cerium (III) Carbonate, Pigment, and/or Dye

In one aspect, the present invention relates to a formulation comprising cerium (III) carbonate and a pigment or a dye or a combination thereof. In one embodiment, the formulation comprises a solvent. Exemplary solvents are described elsewhere herein.

The cerium (III) carbonate can be any cerium (III) carbonate described elsewhere herein and having the properties described elsewhere herein. In one embodiment, the cerium (III) carbonate comprises no electrostatically attached carbonate. In one embodiment, the cerium (III) carbonate releases at least 27.5 wt % $CO_2$ when normalized to the dry weight of the cerium (III) carbonate, during thermogravimetric analysis. In one embodiment, the cerium (III) carbonate is $Ce_2(CO_3)_3 \cdot 4H_2O$ or $Ce_2(CO_3)_3 \cdot 6H_2O$.

The pigment may be any pigment described elsewhere herein. In one embodiment, the pigment is titanium dioxide.

The dye may be any dye described elsewhere herein. In one embodiment, the dye is selected from the group consisting of: iron oxide, carbon black, cadmium sulfide, toluidene red, chrome orange, chrome yellow, chrome green, polyazaindacenes, coumarins, lanthanide complexes, hydrocarbon and substituted hydrocarbon dyes, polycyclic aromatic hydrocarbons, scintillation dyes, aryl- and heteroaryl-substituted polyolefins, carbocyanine dyes, phthalocyanine dyes and pigments, oxazine dyes, carbostyryl dyes, porphyrin dyes, acridine dyes, anthraquinone dyes, anthrapyridone dyes, naphtalimide dyes, benzimidazole derivatives, arylmethane dyes, azo dyes, diazonium dyes, nitro dyes, quinone imine dyes, tetrazolium dyes, thiazole dyes, perylene dyes, perinone dyes, bis-benzoxazolylthiophene, xanthene dyes, indigoid dyes, chromones dyes, flavones dyes, thiazine dyes, and combinations thereof. In one embodiment, the dye is selected from the group consisting of: iron oxide, carbon black, cadmium sulfide, toluidene red, chrome orange, chrome yellow, chrome green, and combinations thereof. In one embodiment, the dye is methylene blue or congo red.

In one embodiment, the cerium (III) carbonate is present in an amount of about 0.005 wt % to about 80 wt % based on the total weight of the formulation. In one embodiment, the cerium (III) carbonate is present in an amount of about 0.005 wt % to about 70 wt % based on the total weight of the formulation. In one embodiment, the cerium (III) carbonate is present in an amount of about 0.005 wt % to about 60 wt % based on the total weight of the formulation. In one embodiment, the cerium (III) carbonate is present in an amount of about 0.005 wt % to about 50 wt % based on the total weight of the formulation. In one embodiment, the cerium (III) carbonate is present in an amount of about 0.005 wt % to about 40 wt % based on the total weight of the formulation. In one embodiment, the cerium (III) carbonate is present in an amount of about 0.005 wt % to about 30 wt % based on the total weight of the formulation. In one embodiment, the cerium (III) carbonate is present in an amount of about 0.005 wt % to about 20 wt % based on the total weight of the formulation. In one embodiment, cerium (III) carbonate is present in an amount of about 0.01 wt % to about 15 wt % based on the total weight of the formulation. In one embodiment, cerium (III) carbonate is present in an amount of about 0.1 wt % to about 10 wt % based on the total weight of the formulation. In one embodiment, cerium (III) carbonate is present in an amount of about 0.1 wt % to about 5 wt % based on the total weight of the formulation.

In one embodiment, the dye is present in an amount from about 0.1 wt % to about 90 wt % of the total weight of the formulation. In one embodiment, the dye is present in an amount from about 0.1 wt % to about 80 wt % of the total weight of the formulation. In one embodiment, the dye is present in an amount from about 0.1 wt % to about 70 wt % of the total weight of the formulation. In one embodiment, the dye is present in an amount from about 0.1 wt % to about 60 wt % of the total weight of the formulation. In one embodiment, the dye is present in an amount from about 0.1 wt % to about 50 wt % of the total weight of the formulation. In one embodiment, the dye is present in an amount from about 0.1 wt % to about 40 wt % of the total weight of the formulation. In one embodiment, the dye is present in an amount from about 1 wt % to about 35 wt % of the total weight of the formulation. In one embodiment, the dye is present in an amount from about 5 wt % to about 30 wt % of the total weight of the formulation.

Pigments and Dyes

Pigments are granular solids incorporated in the formulations described herein. A pigment is a material that changes the color of refracted, reflected, or transmitted light as the result of wavelength-selective absorption. The formulations may contain dyes instead of or in combination with pigments.

Pigments may be classified as either natural or synthetic. Natural pigments include various clays, calcium carbonate, mica, silicas, talcs, graphite or the like, or a combination thereof. Examples of synthetic pigments are titanium dioxide and other titanium pigments, white lead, barium sulfate, calcium carbonate, lithopone, silica, talc, mica, clays, calcined clays, and the so-called reactive pigments which include multivalent metal compounds, such as lead silicochromate, zinc chromate, calcium zinc molybdate, barium metaborate, zinc oxide, zinc sulfide, or the like, or a combination thereof.

Dyes may be used alone or alternatively, in combination with pigments. Examples of dyes are iron oxide, carbon black, cadmium sulfide, toluidene red, chrome orange, chrome yellow, chrome green, polyazaindacenes and/or coumarins, lanthanide complexes, hydrocarbon and substituted hydrocarbon dyes, polycyclic aromatic hydrocarbons, scintillation dyes (e.g., oxazoles and oxadiazoles), aryl- and heteroaryl-substituted polyolefins ($C_2$-$C_8$ olefin portion), carbocyanine dyes, phthalocyanine dyes and pigments, oxazine dyes, carbostyryl dyes, porphyrin dyes, acridine dyes, anthraquinone dyes, anthrapyridone dyes, naphtalimide dyes, benzimidazole derivatives, arylmethane dyes, azo dyes (e.g., Congo Red), diazonium dyes, nitro dyes, quinone imine dyes, tetrazolium dyes, thiazole dyes, perylene dyes, perinone dyes, bis-benzoxazolylthiophene (BBOT), xanthene dyes (e.g., thioxanthene dyes), indigoid dyes (e.g., thioindigoid dyes), chromones dyes, flavones dyes, thiazine dyes (e.g., methylene blue) as well as derivatives comprising at least one of the luminescent tags disclosed herein, or a combination thereof. Luminescent tags also include anti-Stokes shift dyes that absorb in the near infrared wavelength and emit in the visible wavelength.

Solvents

The formulations described herein may comprise a solvent. The solvent may be water, an aqueous solvent (i.e., a solvent that is compatible with water), a water-immiscible solvent, or a combination thereof. Supercritical and/or superheated fluids may also be used as solvents in some formulations. In aspects, the solvent is water. In aspects, the solvent is an aqueous solvent. In embodiments, the solvent is liquid carbon dioxide. Solvents that can be combined with water to form a co-solvent are possible.

The solvents may be liquid aprotic polar solvents, polar protic solvents, non-polar solvents, or combinations thereof. Liquid aprotic polar solvents such as propylene carbonate, ethylene carbonate, butyrolactone, acetonitrile, benzonitrile, nitromethane, nitrobenzene, sulfolane, dimethylformamide, N-methylpyrrolidone, or the like, or combinations thereof are generally desirable for dissolving the template. Polar protic solvents such as, water, methanol, acetonitrile, nitromethane, ethanol, propanol, isopropanol, butanol, or the like, or combinations thereof may be used. Other non-polar solvents such a benzene, toluene, methylene chloride, carbon tetrachloride, hexane, diethyl ether, tetrahydrofuran, or the like, or combinations thereof may also be used to dissolve the template. Examples of preferred solvents are water, alcohols, acetone, or a combination thereof. The most preferred solvent is water.

Processes of Producing Cerium (III) Carbonate

The disclosure provides processes for producing cerium (III) carbonate by (i) mixing a carbonate salt and water to form a first solution; (ii) mixing a cerium (III) salt and water to form a second solution; (iii) mixing the first solution and the second solution to form a third solution having a pH of 9.2 or less; and (iv) centrifuging the third solution to form the cerium (III) carbonate described herein. In aspects, the third solution has a pH from about 9.0 to 9.2 or less. In aspects, the third solution has a pH of about 9.1. In aspects, the third solution has a pH of about 9.0. In aspects, in order to achieve the pH values, a sufficiently rapid mixing time is required when mixing the first and the second solution to form the third solution. In aspects, the mixing time is about 4 minutes or less. In aspects, the mixing time is about 3 minutes or less. In aspects, the mixing time is about 2 minutes or less. In aspects, this mixing time is about 1 minute or less. In aspects, this mixing time is about 45 seconds or less. In aspects, this mixing time is about 30 seconds or less. In aspects, this mixing time is about 20 seconds or less. In aspects, this mixing time is about 15 seconds or less. In aspects, this mixing time is about 10 seconds or less. In aspects, the mixing time is from about 10 seconds to about 90 seconds. In aspects, the mixing time is from about 10 seconds to about 60 seconds. In aspects, the mixing time is from about 15 seconds to about 60 seconds. In aspects, the mixing time is from about 15 seconds to about 45 seconds. In aspects, the mixing time is from about 15 seconds to about 30 seconds. In aspects, the mixing time is from about 15 seconds to about 20 seconds. It has been unexpectedly discovered that when the pH is greater than than a threshold around 9.2, or alternatively, when the mixing time is greater than that described herein (e.g., more than 1 minute), the resulting cerium (III) carbonate will not be white; instead, it will have a yellowish tint due to the presence of cerium (IV) species. In aspects, the cerium (III) carbonate used in the processes described herein is a cerium (III) carbonate source material as described in detail herein. In aspects, the cerium (III) carbonate is $Ce_2(CO_3)_3.4H_2O$. In aspects, the carbonate salt is a solid. In aspects, the carbonate salt is ammonium carbonate, aluminum carbonate, sodium carbonate, potassium carbonate, hydrogen carbonate, and the like. In aspects, the cerium (III) salt is ammonium cerium (III) nitrate, ammonium cerium (III) nitrate tetrahydrate, cerium (III) bromide, cerium (III) bromide hydrate, cerium (III) chloride, cerium (III) chloride heptahydrate, cerium (III) fluoride, cerium (III) iodide, cerium (III) nitrate, cerium (III) nitrate hexahydrate, cerium (III) oxalate hydrate, cerium (III) sulfate, cerium (III) sulfate hydrate, cerium (III) sulfate octahydrate, and the like. The amount of each component to use in the process can be determined by the skilled artisan with reference to the working examples herein.

The disclosure provides processes for producing cerium (III) carbonate by (i) mixing ammonium carbonate and ammonium cerium (III) nitrate tetrahydrate to form a first solution; (ii) washing the first solution with water; and (iii) centrifuging to recover the cerium (III) carbonate from suspension. In aspects, the cerium (III) carbonate is $Ce_2(CO_3)_3.4H_2O$. In aspects, the cerium (III) carbonate is a cerium (III) carbonate source material as described in detail herein. In aspects, the cerium (III) carbonate releases at least 28.0 wt % $CO_2$ when normalized to the dry weight of the cerium (III) carbonate, during thermogravimetric analysis. In aspects, the cerium (III) carbonate releases at least 28.5 wt % $CO_2$ when normalized to the dry weight of the cerium (III) carbonate, during thermogravimetric analysis. In embodiments, the cerium (III) carbonate releases at least 29.0 wt % $CO_2$ when normalized to the dry weight of the cerium (III) carbonate source material, during thermogravimetric analysis. The amount of each component to use in the process can be determined by the skilled artisan with reference to the working examples herein.

The disclosure provides processes for producing cerium (III) carbonate by (i) mixing ammonium carbonate and water to form a first solution; (ii) mixing ammonium cerium (III) nitrate tetrahydrate and water to form a second solution; (iii) mixing the first solution and the second solution to form a third solution of pH 9.2 or less; and (iv) centrifuging the third solution to form the cerium (III) carbonate described herein. In aspects, the third solution has a pH from about 9.0 to 9.2 or less. In aspects, the third solution has a pH of about 9.1. In aspects, the third solution has a pH of about 9.0. In aspects, in order to achieve the pH values, a sufficiently rapid mixing time is required when mixing the first and the second solution to form the third solution. In aspects, the mixing time is about 4 minutes or less. In aspects, the mixing time is about 3 minutes or less. In aspects, the mixing time is about 2 minutes or less. In aspects, this mixing time is about 1 minute or less. In aspects, this mixing time is about 45 seconds or less. In aspects, this mixing time is about 30 seconds or less. In aspects, this mixing time is about 20 seconds or less. In aspects, this mixing time is about 15 seconds or less. In aspects, this mixing time is about 10 seconds or less. In aspects, the mixing time is from about 10 seconds to about 90 seconds. In aspects, the mixing time is from about 10 seconds to about 60 seconds. In aspects, the mixing time is from about 15 seconds to about 60 seconds. In aspects, the mixing time is from about 15 seconds to about 60 seconds. In aspects, the mixing time is from about 15 seconds to about 45 seconds. In aspects, the mixing time is from about 15 seconds to about 30 seconds. In aspects, the mixing time is from about 15 seconds to about 20 seconds. In aspects, the cerium (III) carbonate releases at least 28.5 wt % $CO_2$ when normalized to the dry weight of the cerium (III) carbonate, during thermogravimetric analysis. In embodiments, the cerium (III) carbonate releases at least 29.0 wt % $CO_2$ when normalized to the dry weight of the cerium (III) carbonate source material, during thermogravimetric analysis. In aspects, the cerium (III) carbonate is $Ce_2(CO_3)_3 \cdot 4H_2O$. In aspects, the cerium (III) carbonate is a cerium (III) carbonate source material as described in detail herein. The amount of each component to use in the process can be determined by the skilled artisan with reference to the working examples herein.

In aspects of the processes described herein, step (iii) comprises vigorously mixing the first solution and the second solution from about 5 minutes to about 2 hours; or from about 30 minutes to about 90 minutes; or from about 45 minutes to about 75 minutes; or about 60 minutes. In aspects, step (iv) comprises centrifuging the third solution from about 5,000 rpm to about 30,000 rpm, for about 1 minute to about 30 minutes, at a temperature from about 5° C. to about 30° C. In aspects, step (iv) comprises centrifuging the third solution from about 10,000 rpm to about 20,000 rpm, for about 1 minute to about 5 minutes, at a temperature from about 10° C. to about 20° C. In aspects, step (iv) comprises centrifuging the third solution at about 15,000 rpm for about 3 minutes at a temperature of about 15° C. The process further comprises vortexing and sonicating the third solution in water before centrifuging the third solution to obtain the cerium (III) carbonate. In aspects, the process further comprises vortexing the third solution for about 1 minute to about 10 minutes, and then sonicating the third solution for about 1 minute to about 10 minutes, where the vortexing and sonicating are conducted in water, before centrifuging the third solution to obtain the cerium (III) carbonate. In aspects, the process further comprises vortexing the third solution for about 5 minutes, and then sonicating the third solution for about 5 minute, where the vortexing and sonicating are conducted in water, before centrifuging the third solution to obtain the cerium (III) carbonate.

In one embodiment, the disclosure provides a process for preparing cerium (III) carbonate comprising the step of mixing in the presence of water, a) ammonium carbonate and b) ammonium cerium (III) nitrate. The ammonium carbonate and ammonium cerium (III) nitrate can be mixed in any fashion known to a person of skill in the art. Exemplary mixing methods are described elsewhere herein. Exemplary mixing times are further described elsewhere herein. In one embodiment, the ammonium carbonate and ammonium cerium (III) nitrate are mixed at room temperature. In one embodiment, the ammonium carbonate and ammonium cerium (III) nitrate are mixed in the presence of water at a pH of from about 9.0 to 9.2. In one embodiment, the cerium (III) carbonate prepared by this process comprises no electrostatically attached carbonate. In one embodiment, the cerium (III) carbonate prepared by this process releases at least 27.5 wt % $CO_2$ when normalized to the dry weight of the cerium (III) carbonate, during thermogravimetric analysis.

The disclosure provides cerium (III) carbonate produced by the processes described herein. In aspects, the cerium (III) carbonate releases at least 28.4 wt % $CO_2$ when normalized to the dry weight of the cerium (III) carbonate, during thermogravimetric analysis. In aspects, the cerium (III) carbonate releases at least 28.5 wt % $CO_2$ when normalized to the dry weight of the cerium (III) carbonate source material, during thermogravimetric analysis. In aspects, the cerium (III) carbonate releases at least 29.0 wt % $CO_2$ when normalized to the dry weight of the cerium (III) carbonate source material, during thermogravimetric analysis. In aspects, the cerium (III) carbonate is the cerium (III) carbonate source material described herein. In aspects, the cerium (III) carbonate is $Ce_2(CO_3)_3 \cdot 4H_2O$.

Processes for Producing Formulations

The formulations described herein may be manufactured by a variety of different methods, such as those exemplified herein. The formulations may be manufactured in a batch process, in a continuous process, or in a combination thereof.

In embodiments, the cerium (III) carbonate source material is added as a powder or wet paste directly to the formulations. The powder is then blended into the formulation using a variety of different forces.

Blending of the cerium (III) carbonate into the formulations may involve the use of at least one of shear forces, extensional forces, compressive forces, ultrasonic energy, electromagnetic energy, thermal energy or a combination comprising at least one of the foregoing forces or forms of energy and is conducted in processing equipment wherein the aforementioned forces are exerted by a single screw, multiple screws, intermeshing co-rotating or counter rotating screws, non-intermeshing co-rotating or counter rotating screws, reciprocating screws, screws with pins, barrels with pins, rolls, rams, helical rotors, or combinations comprising at least one of the foregoing.

Blending involving the aforementioned forces may be conducted in machines such as single or multiple screw extruders, Buss kneader, Henschel, helicones, Ross mixer, Banbury, roll mills, molding machines such as injection molding machines, vacuum forming machines, blow molding machine, high-shear mixer, speed mixer, or then like, or combinations comprising at least one of the foregoing machines.

In embodiments, the cerium (III) carbonate is first mixed with a portion of the organic compound susceptible to photodegradation to form a masterbatch. The masterbatch may be in the form of a paste or may be in the form of pellets. The masterbatch is then added to the remainder of the composition (such as the solvent (e.g., water), the photocatalytically active pigment, and other ingredients) to form the final formulation.

In embodiments, the masterbatch is generally manufactured in a first batch mixer such as a Banbury, a Waring blender, a Henschel mixer, a Ross mixer, or the like. The masterbatch may be blended into the final composition in a second batch mixer. In embodiments, the first batch mixer may be different from the second batch mixer. In embodiments, the first batch mixer may be the same as the second batch mixer.

In embodiments, the masterbatch is manufactured in a first batch process (described above), or alternatively, in a first continuous process. The masterbatch is then let down into the final formulation in a second continuous process. Continuous processes include single and/or twin screw extruders.

In embodiments, the masterbatch is manufactured in a continuous process, while the formulation (the mixing of the masterbatch with the remainder of the paint composition) is manufactured in a batch process.

In one embodiment, the disclosure provides a process for preparing a composition comprising cerium (III) carbonate and a dye or a pigment or a combination thereof. In one embodiment, the process of preparing this composition comprises the steps of: (i) mixing in the presence of water, a) ammonium carbonate and b) ammonium cerium (III) nitrate, forming cerium (III) carbonate; and (ii) mixing the prepared cerium (III) carbonate with a dye or a pigment or a combination thereof. In one embodiment, the ammonium carbonate and ammonium cerium (III) nitrate are mixed in the presence of water at a pH of from about 9.0 to 9.2.

The cerium carbonate prepared by this process can have any properties described elsewhere herein. The cerium (III) carbonate can be mixed with any dye and/or pigment described elsewhere herein. In one embodiment, the prepared cerium (III) carbonate is mixed in step (ii) with titanium dioxide. In one embodiment, the prepared cerium (III) carbonate is mixed in step (ii) with a dye selected from the group consisting of: iron oxide, carbon black, cadmium sulfide, toluidene red, chrome orange, chrome yellow, chrome green, and combinations thereof. In one embodiment, the prepared cerium (III) carbonate is mixed in step (ii) with a dye selected from congo red or methylene blue. In one embodiment, the wt. % of cerium (III) carbonate in the composition is described elsewhere herein. In one embodiment, the wt. % of pigment in the composition is described elsewhere herein. In one embodiment, the wt. % of dye in the composition is described elsewhere herein.

EXAMPLES

The following examples are for purposes of illustration and are not intended to limit the spirit or scope of the disclosure or claims.

Example 1

Synthesis of the insoluble Ce (III) compound by precipitating Ce (III) on P25 photocatalytically active pigment. This example compares the photopassivation effectiveness of a cerium (III) compound that is dissolved in the solvent (ammonium cerium (III) nitrate) versus those that are micro-precipitated proximate to oxide-pigment surfaces.

Step A.
Preparation of an Aqueous Mixture of Ammonium Cerium (III) Nitrate Tetrahydrate and Ammonium Carbonate.

To a plastic vial 0.52 grams (g) of solid ammonium carbonate was added and mixed with 2.65 milliliters (mL) deionized (DI) water to obtain a clear solution. Separately, 87.7 mg of ammonium cerium (III) nitrate tetrahydrate was added into 3.5 mL DI water and vortexed (stirred) for 30 seconds (sec) to obtain a transparent solution. Thereafter, the Ce (III) salt containing aqueous solution (i.e., ammonium cerium (III) nitrate tetrahydrate) was added into ammonium carbonate solution under vigorous stirring and $N_2$ flow. The pH of the resulting solution was around pH 9.1±0.1. This solution was directly used to prepare a mixture with P25.

Step B.
Pre-Treatment of P25 with TAMOL™ 1124

6 g of P25, 68 microliters (μL) TAMOL™ 1124, and 10 mL water were added into a round bottom flask and stir for 1 hour (h) at 500 revolutions per minute (rpm). TAMOL™ 1124 (a hydrophilic copolymer polyelectrolyte) was obtained from the DOW Chemical Company and is a pigment dispersant. It is a hydrophilic copolymer that is used in a wide range of latex paint formulations from high gloss enamels to low sheen flats. It provides stability and compatibility with latex paint additives. It provides compatibility with pigments for good color acceptance and is low foaming for ease of use. The resulting mixture was centrifuged at 14000 rpm for 5 minutes (min). The centrifuged product was washed with 100 mL DI water to remove excess TAMOL™ 1124 and re-centrifuged at 1400 rpm for 5 min. Washing and centrifugation were repeated one more time, and the final product was stored as a wet paste having a solid weight content of 48.1 wt %, based on the total weight of the paste.

Step C.
Precipitation of Ce (III) on P25 Pigment Photocatalyst

Ce (III) precursor solution obtained in above was added into a plastic vial having 2.08 g of TAMOL™-treated wet paste (48.07 wt %) of P25, as obtained above. The resulting paste was subjected to high shear mixing at 3500 rpm, and turned into a slurry, which was subsequently stirred for 1 h. Afterwards, the mixture was centrifuged at 14000 rpm for 5 min, and the product washed with 100 mL DI water including 5 min vortex mixing, prior to re-centrifugation. Washing and centrifugation cycles were repeated for two more times, and the product was stored as a wet paste called Ce (III)-P25. The Ce (III)-P25 wet paste was dried in a lyophilizer for 16 h prior to its use in photo-passivation experiments.

Comparative study of rate of methylene-blue organic dye photodegradation using dissolved cerium (III) ammonium nitrate salt in aqueous solution versus a cerium (III) compound micro-precipitated proximate to the oxide-pigment surface of P25 (i.e. Ce (III)-P25), in the presence of the same amount of unmodified P25.

This experiment was conducted to demonstrate the inhibition of photodegradation processes of organic molecules with an insoluble cerium (III) compound. To evaluate the inhibition of photodegradation processes of organic molecules (such as methylene-blue (MB) dye) associated with photogenerated reactive oxygen species (ROS) in the presence of P25, a soluble cerium (III) salt in an aqueous solution (i.e. cerium (III) ammonium nitrate tetrahydrate) was also used as a ROS scavenger.

Thus, two separate aqueous solutions of ammonium cerium (III) nitrate were prepared, by dissolving 2.5 mg in 9.9 mL of DI water, and another consisting of 10 milligrams (mg) of ammonium cerium (III) nitrate in 9.9 mL water. The pH of both solutions was adjusted to pH 9.1 using ammonium hydroxide ($NH_4OH$). The respective solutions were each stirred for 15 min, and 0.1 mL of $10^{-3}$ molar (M) MB organic dye was added into each ammonium cerium (III) nitrate solution, so as to maintain the MB dye concentration at $10^{-5}$ M in both solutions. 1 mg of P25 powder was added to each solution. Each resulting solution now containing P25, MB organic dye, and ammonium cerium (III) nitrate was separately irradiated using 254 nm ultraviolet (UV) light (150 lumens) under an enclosed photoreactor at 25° C.

After equal intervals of UV light exposure, aliquots were taken from the reaction mixture and centrifuged to remove the photocatalyst. The amount of residual MB organic dye remaining was quantified via UV-Visible spectrophotometry of the supernatant liquid, and these data points are shown in the graphs in FIG. 1 as −lnA vs time plots (where A represents "concentration"), in order to represent a pseudo first-order rate constant for the MB organic dye photodegradation.

Figure 1B:
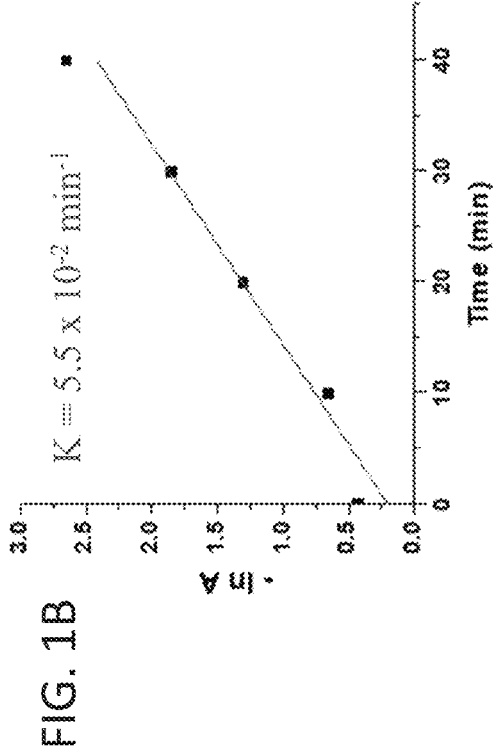
FIGS. 1A-1C are plots of MB dye photodegradation under 254 nm light at pH 9.1 using 1 mg of P25 photocatalyst in presence of: (i) 2.5 mg of soluble (dissolved) ammonium cerium(III) nitrate (FIG. 1A); (ii) 10 mg soluble (dissolved) ammonium cerium(III) nitrate (FIG. 1B): and (iii) 1 mg of insoluble Ce(III)-P25 (FIG. 1C).
Figure 1C:
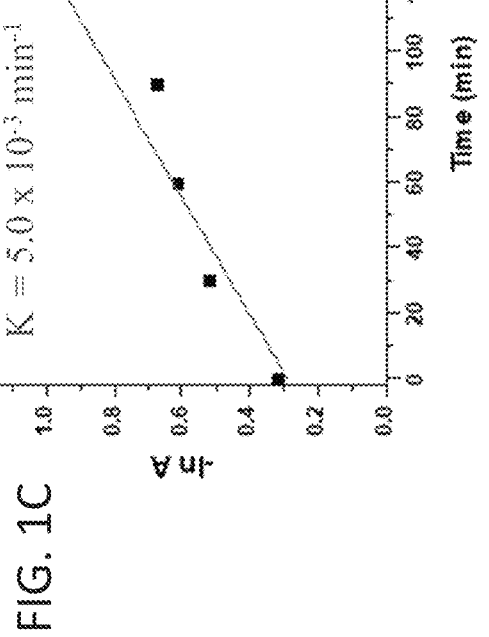
Figure 1A:
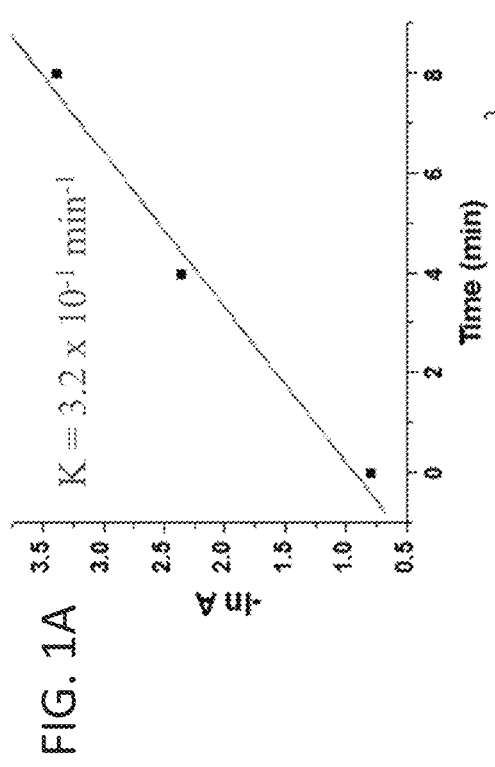

A separate photocatalysis experiment was performed using a combination of 1 mg of P25 and 1 mg of insoluble Ce (III)-P25, which represents the cerium (III) compound precipitated on the surface of the oxide-pigment photocatalyst. In this photocatalysis experiment, there were no soluble cerium (III) salts present. The efficiency of P25 photopassivation was compared with the system using the water-soluble cerium (III) salt (the soluble cerium (III) nitrate), in terms of the rate of MB organic dye photodegradation. The results are shown in the FIGS. 1A-1C. FIG. 1A is a graph of MB dye photodegradation under 254 nm light at pH 9.1 using 1 mg of P25 in presence of 2.5 mg of soluble (dissolved) ammonium cerium (III) nitrate. FIG. 1B is a graph of MB dye photodegradation under 254 nm light at pH 9.1 using 1 mg of P25 photocatalyst in presence of 10 mg of soluble (dissolved) ammonium cerium (III) nitrate. FIG. 1C is a graph of MB dye photodegradation under 254 nm light at pH 9.1 using 1 mg of P25 in presence of 1 mg of insoluble Ce (III)-P25.

The data in FIG. 1A shows a higher rate of MB dye photodegradation with 1 mg P25 in the presence of 2.5 mg of soluble cerium (III) ammonium nitrate salt, with the calculated rate constant for dye degradation being 0.32 $min^{-1}$. When the amount of soluble cerium (III) ammonium nitrate was increased by a factor of 4 (now up to 10 mg) in FIG. 1B, the rate of dye degradation decreased by a factor of about 6, to yield a rate constant of $5.5 \times 10^{-2}$ $min^{-1}$. When Ce (III)-P25 (with the cerium (III) carbonate) was used for the inhibition of MB organic dye, the amount of MB organic dye photodegradation with nearly 2 mg of P25 total (instead of 1 mg as in studies involving soluble salts above) exhibited a 64-fold decrease (rate=$5 \times 10^{-3}$ $min^{-1}$ (see FIG. 1C) in the MB dye photodegradation rate relative to that obtained when using 2.5 mg of cerium (III) soluble salt above. Thus even when the amount of photocatalyst is doubled, the rate of degradation of the organic MB dye is substantially lower when an insoluble cerium (III) compound is used especially when compared with a composition that contains a soluble cerium salt and a smaller amount of photocatalyst.

If it is assumed that during synthesis of Ce (III)-P25 (that contains the insoluble cerium (III) compound), the maximum possible theoretical amount of cerium (III) was precipitated proximate to the surface of the P25 photocatalyst, then it would provide 87.7 mg of ammonium cerium (III) nitrate for 1 g of P25. This means that the 1 mg Ce (III)-P25 utilized for the photocatalysis experiment above contains only 0.087 mg ammonium cerium (III) nitrate by weight. This amount of cerium (III) compound is 29-fold and 115-fold smaller than what would be present in the 2.5 mg and 10 mg of water soluble ammonium cerium (III) nitrate, respectively. However, the inhibitive effect of the insoluble cerium (III) compound towards the photodegradation of the MB organic dye is much greater than when the cerium (III) compound is soluble.

Without being limited to theory, it is believed that this could be the result of a much higher effectiveness for photopassivation when using an insoluble cerium (III) compound versus a soluble one, or, alternatively, the effect of proximity between the cerium (III) compound and the surface of the oxide-pigment photocatalyst. The effect of the latter is investigated in Example 3.

These results demonstrate that there is a great advantage in terms of photopassivation efficiency, when using an insoluble cerium (III) compound. This photopassivation functions in the example above even when there is no contact between the cerium (III) compound and the P25 (i.e., roughly half of the P25 in the example above did not consist of cerium (III) compound contacting its surface, but rather consisted of bare P25 in the absence of cerium (III) compound). It was surprisingly and unexpectedly discovered that the cerium (III) compound at-a-distance from this bare P25 was able to quench its photoactivity efficiently. In other words, quenching of photoactivity of a photocatalyst by a cerium (III) compound without contact between the cerium (III) compound and photocatalyst is a synergistic effect that was not previously observed.

While the aforementioned example surprisingly demonstrates the photopassivation effectiveness of a cerium (III) compound when not in contact with the photocatalyst (i.e., located proximate to the photocatalyst while not contacting it), it can be further demonstrated that photopassivation via an action-at-a-distance mechanism works in compositions that include other oxide pigments or fillers.

To demonstrate the effect with other pigments, cerium (III) compound was also precipitated in the presence of $SiO_2$ nanoparticles, in the presence of rutile $TiO_2$ (particle size of 300 nm), in the presence of commercial pigments such as Ti-Pure R706 (particle size of 300 nm; which themselves exhibit some photocatalytic activity) (see Example 2), in a similar fashion as the cerium (III) compound was precipitated in the presence of P25 above. In addition to Ce (III) precipitation in the presence of oxides, a separate insoluble phase of Ce (III) compound was prepared (see Example 3), which is even more effective at inhibiting the photodegradation of organics in slurries containing the photocatalyst.

All of these examples, i.e., containing Ce (III)-modified $SiO_2$, Ce (III)-modified $TiO_2$, or Ce (III)-modified Ti-R706 and a separate phase of cerium (III) compound within the dispersion demonstrate inhibition of photodegradation of organic dye, to a significantly greater extent than the soluble cerium (III) ammonium nitrate (vide infra), and surprisingly do so by an action-at-a-distance mechanism (meaning no physical contact between photocatalyst and cerium (III) compound is seen).

Insoluble Ce (III) compound by precipitating cerium (III) compound on $SiO_2$ (having a $SiO_2$ particle size 20 nm to 60 nm):

Synthesis:

The precipitation of the cerium (III) compound proximate to $SiO_2$ was performed in a similar manner to Example 1 above, except for a few following changes: (i) in Step A above of the synthesis, 0.52 g ammonium carbonate was dissolved in 5 mL water (instead of 2.63 mL as in Example 1), and 1 g (instead of 87.7 mg) of ammonium cerium (III) nitrate tetrahydrate was dissolved in 18 mL water; (ii) in Step B above, in place of P25, 1 g of $SiO_2$ powder (average particle size of 20 nm to 60 nm was obtained from Skyspring Nanomaterials Inc) was added into a plastic container containing 10 µL TAMOL™ 1124 and 10 mL DI water and stirred for 1 h at 500 rpm; (iii) in Step C above, the mixture of ammonium Ce (III) nitrate and ammonium carbonate (obtained in Step A above) having pH of 9.1±0.1 was introduced to a $SiO_2$ wet paste (obtained in Step B above) instead of P25 and eventually the cerium (III) carbonate was precipitated on $SiO_2$. The final product obtained was dried in a lyophilizer for 16 h, and the dried product appeared brilliant white in color (see FIG. 2A).

Figure 2B:
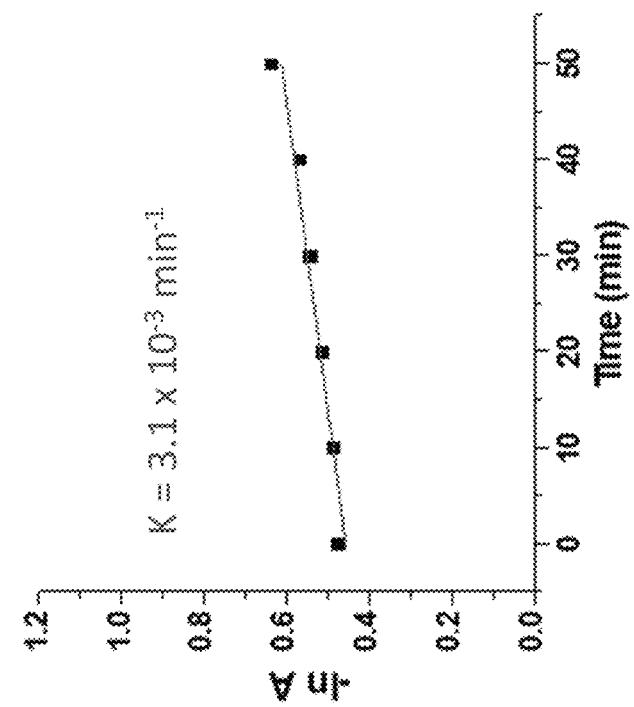
FIGS. 2A-2B.
Figure 2A:
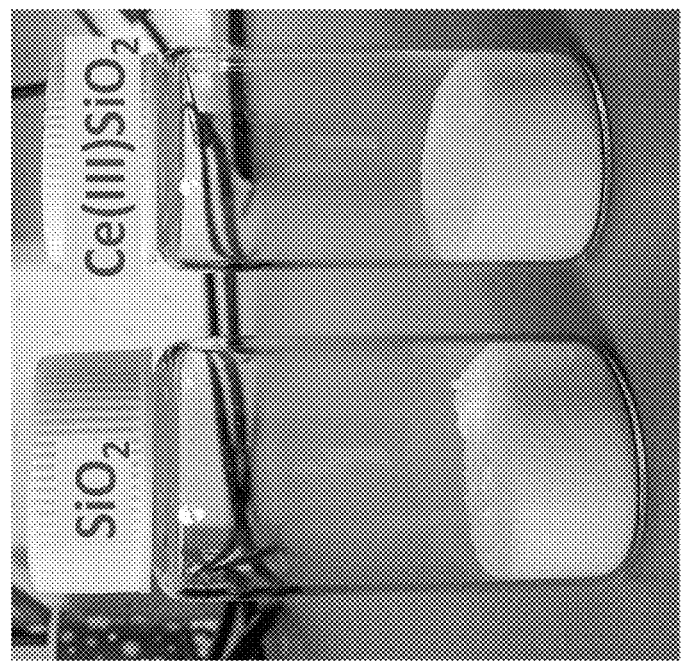

Photostabilization of MB organic dye using Ce (III)-$SiO_2$: FIG. 2B is a graph of –ln A vs time that shows the pseudo first order plot of 10 mL $10^{-5}$ M MB organic dye photodegradation performed with 50 mg of P25 photocatalyst in presence of 5 mg of Ce (III)-$SiO_2$, and the rate constant for MB organic dye degradation calculated from this plot is found to be $3.1 \times 10^{-3}$ $min^{-1}$. If it is assumed that during synthesis of Ce (III)-$SiO_2$, the maximum possible amount of cerium (III) compound has been precipitated proximate to the surface of $SiO_2$, then it would provide 1 g of ammonium cerium (III) nitrate for 1 g of $SiO_2$. This means 1 mg Ce (III)-$SiO_2$ utilised for the photocatalytic degradation of MB organic dye could contain a maximum of up to 1 mg of ammonium cerium (III) nitrate. This amount of cerium (III) is 2.5-fold and 10-fold smaller than was present in 2.5 mg and 10 mg of water soluble ammonium cerium (III) nitrate, respectively, in Example 1 above.

However, according to data in FIG. 2B, the rate of photodegradation of MB organic dye with Ce (III)-$SiO_2$ is observed to be decreased 103 fold and 18 fold relative to the rate of MB organic dye photodegradation obtained in the presence of 2.5 mg and 10 mg of soluble ammonium cerium (III) carbonate respectively in Example 1. It is notable that MB organic dye photodegradation with soluble ammonium cerium (III) nitrate was performed in the presence of only 1 mg of P25, which is a 55-fold lower amount of photocatalyst compared to that used here with Ce (III)-$SiO_2$ as passivating agent.

Based on the data in FIG. 2B, the aqueous soluble cerium (III) nitrate is a significantly less effective photopassivating agent compared to insoluble cerium (III) compound used in the Ce (III)-$SiO_2$. Moreover, the mechanism of action of the latter material as a photopassivant is via an action-at-a-distance mechanism, in which the effect of the Ce (III)-$SiO_2$ as photopassivant does not require contact with the P25 surface.

Figure 3A:
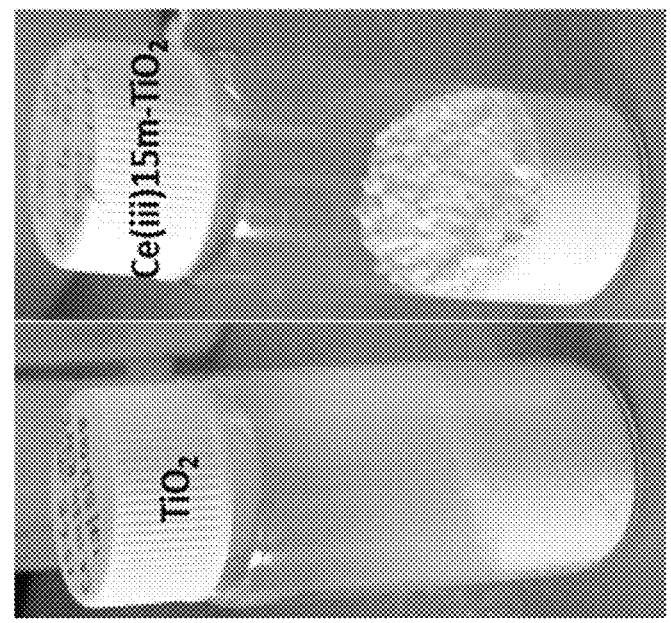
FIGS. 3A-3B.

Photopassivation of MB organic dye using Ce (III)-$TiO_2$—a commercial grade pure rutile titania (particle size 300 nm) in the presence of which Ce (III) has been precipitated so as to form a solid mixture comprising rutile and cerium (III) carbonate:

Synthesis:

The precipitation of cerium (III) compound proximate to $TiO_2$ was performed similar to Example 1, except for the following changes: (i) in Step A of the synthesis, 0.52 g ammonium carbonate is dissolved in 5 mL water (instead of 2.63 mL in example 1) and 1 g of ammonium cerium (III) nitrate tetrahydrate (instead of 87.7 mg used in example 1) was dissolved in 18 mL water; (ii) in Step B of the synthesis, in place of P25, 100 g of $TiO_2$ powder (pure rutile, without any photopassivating layer having an average particle size of 300 nm obtained from US Research Nanomaterials Inc) was added into a round bottom flask containing 1 mL TAMOL™ 1124 and 100 mL DI water, and stirred for 1 h at 500 rpm; (iii) in Step C, the mixture of ammonium cerium (III) nitrate and ammonium carbonate (obtained in Step A) was introduced in a 73 wt % aqueous slurry containing 11.4 g of $TiO_2$ powder (instead of P25 used in Example 1) and stirred for 1 h prior to centrifugation and washing. The final product obtained was dried in a lyophilizer for 16 h, to yield a dried product that is white in color with a pale off-white tint, as shown in FIG. 3A.

Figure 3B:
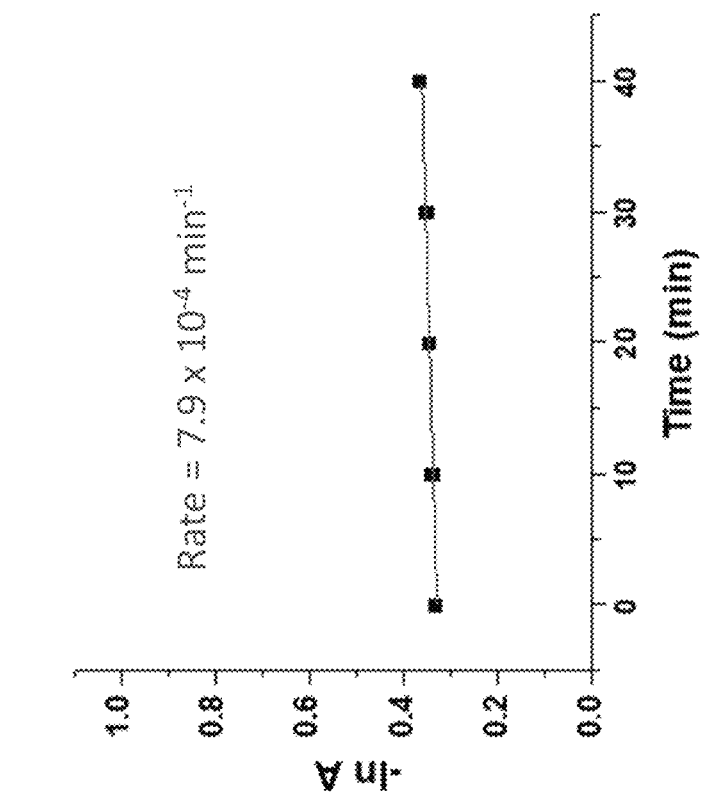

FIG. 3B is a graph of ln A vs time that shows the pseudo first order plot for the degradation of $10^{-5}$ M MB organic dye, which was performed in a 10 mL aqueous slurry consisting of 2 mg of P25 in presence of 5.7 mg of Ce (III)-$TiO_2$ (i.e., 1:0.8 surface area ratio of P25 and Ce (III)-$TiO_2$). The rate constant for MB organic dye photodegradation calculated from data in FIG. 3B is $7.9 \times 10^{-4}$ $min^{-1}$. Elemental analysis by neutron activation analysis showed that Ce (III)-$TiO_2$ contains 4.35 wt % cerium relative to $TiO_2$ by weight. This means 5.7 mg Ce (III)-$TiO_2$ utilised for the photocatalysis of MB dye contains 0.245 mg of cerium, in comparison to the 0.625 mg and 2.5 mg of cerium contained in 2.5 mg and 10 mg of water-soluble ammonium cerium (III) nitrate, respectively.

A 400-fold and 69-fold decrease in the rate constant for MB organic dye photodegradation is observed when using Ce (III)-$TiO_2$ relative to 2.5 mg and 10 mg of soluble ammonium cerium (III) carbonate, despite the much larger amount of cerium in the soluble cases than when using the insoluble cerium (III) compound used in Ce (III)-$TiO_2$.

Accordingly, aqueous soluble ammonium cerium (III) nitrate is a significantly less effective photopassivating agent compared to cerium (III) carbonate precipitated on rutile $TiO_2$. Further surprisingly, the action of the latter material as a photopassivant must be through an action-at-a-distance mechanism, since the P25 is located on a different particle than the one onto which the insoluble Ce (III)-compound is precipitated proximate to.

Example 2

Significance of the Ce (III):Ce (IV) Molar Ratio being Greater than Unity (i.e., Greater than 1) in the Cerium (III) Compound Used for Photopassivation Synthesis:

Precipitation of cerium (III) proximate to Ti-Pure R706 was performed in a manner similar to Example 1 above, except for the following changes: (i) in Step A above of the synthesis, 0.52 g ammonium carbonate was dissolved in 5 mL water (instead of 2.63 mL in Example 1) and 1 g of ammonium cerium (III) nitrate tetrahydrate was dissolved in 18 mL water; (ii) in Step B, in place of P25 photocatalyst, 100 g of Ti-Pure R706 powder (having an average particle size of 300 nm and was obtained from The Chemours company) was added into a round bottom flask containing 1 mL TAMOL™ 1124 and 100 mL DI water, and the resulting suspension was stirred for 1 h at 500 rpm; (iii) in Step C above, the mixture of ammonium cerium (III) nitrate and ammonium carbonate (obtained in Step A) having pH of 9.1±0.1 was introduced in a 73 wt % aqueous slurry containing 11.4 g of R706 (instead of P25 used in Example 1), and the resulting slurry was stirred for 1 h prior to centrifugation and washing. The final product, Ce (III)-R706, which represents cerium (III)-modified Ti-Pure R706, was obtained by drying in a lyophilizer for 16 h, to yield a brilliant white powder, as shown in the FIG. 4B. FIG. 4A is a picture that shows the Ti-Pure R706 prior to the modification with the insoluble cerium (III) compound. There is virtually no color difference between the modified and unmodified Ti-Pure R706.

Photodegradation of MB Organic Dye in Aqueous Solution (Under 254 nm Light) with P25 Photocatalyst in Presence of Ce (III)-R706 Versus Unmodified Ti-Pure R706.

Figure 5A:
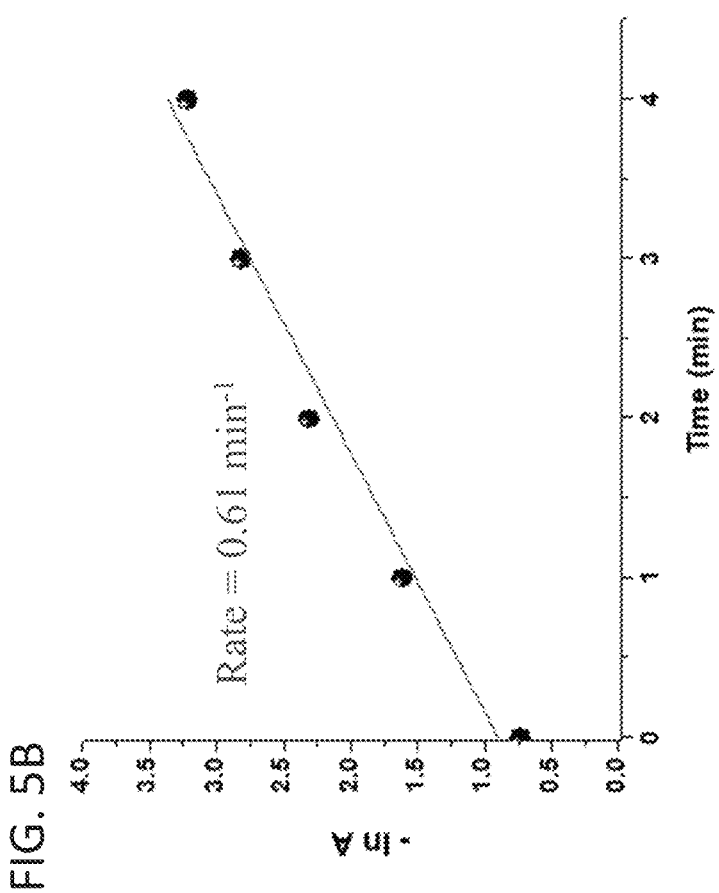
FIGS. 5A-5B are plots of kinetics of $10^{-5}$ M MB organic dye degradation with P25 in presence of Ce(III)1h-R706 (FIG. 5A) and unmodified R706 (FIG. 5B).

The photocatalytic degradation of MB organic dye was performed in an aqueous slurry consisting of 1 mg of P25 photocatalyst in the presence of 5.7 mg of either Ce (III)-R706 or unmodified (i.e., no cerium (III) compound was added) Ti-Pure R706. This results in an equivalent surface area of P25 and either Ce (III)-R706 or Ti-Pure R706, since the surface area of P25 is 57 $m^2/g$ and that of R706 is 10 $m^2/g$. The results are shown in the FIGS. 5A and 5B. FIG. 5A is a plot of −ln A vs time for the MB organic dye degradation with P25 in presence of Ce(III)-R706, while FIG. 5A is a plot of −ln A vs time for the MB organic dye degradation with P25 in presence of the unmodified R706.

Figure 5B:
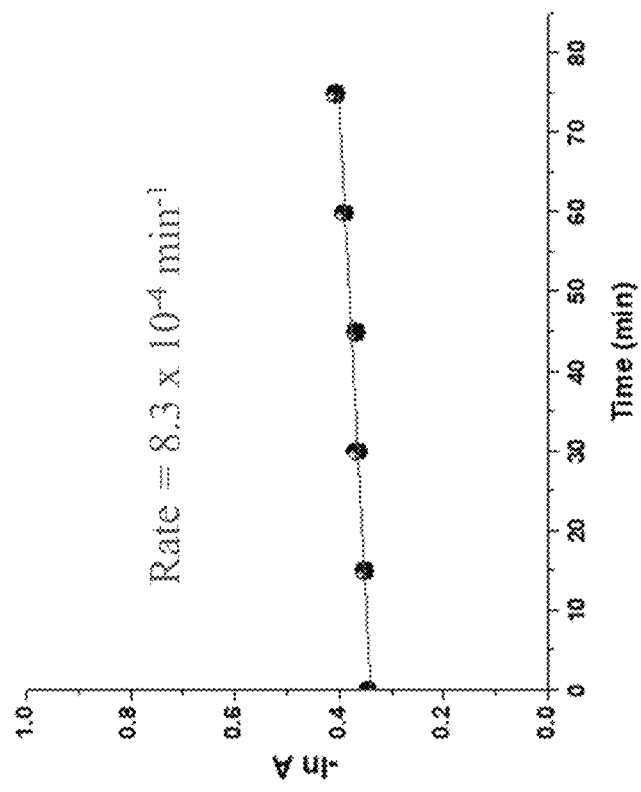

Data shown in the FIGS. 5A and 5B demonstrates that the rate constant for MB organic dye photodegradation decreased from 0.61 $min^{-1}$ (for the case of Ti-Pure R706 added to slurry in the FIG. 5B) down to $8.3 \times 10^{-4}$ $min^{-1}$ (for the case of Ce (III)-R706 added to slurry in the FIG. 5A). These results demonstrate that unmodified Ti-Pure R706 on its own is unable to effectively quench photocatalysis of P25 photocatalyst, in the way that Ce (III)-R706 can. Photodegradation of MB organic dye in aqueous solution (under 254 nm light) with P25 photocatalyst in presence of Ce (III)-R706 versus a variant that contains a mixed-valence Ce (III)/Ce (IV)-R706 material, in which an equimolar mixture of cerium (III) and cerium (IV) have been precipitated proximate to the surface of Ti-Pure R706.

Figure 6B:
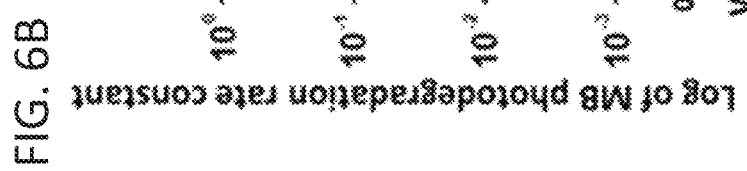
FIGS. 6A-6B are plots of kinetics of $10^{-5}$ M MB organic dye degradation in presence varied fraction of P25 and Ce(III)-R706 (FIG. 6A) and varied fraction of P25 and Ce(III)/Ce(IV-R706) (FIG. 6B)
Figure 6A:
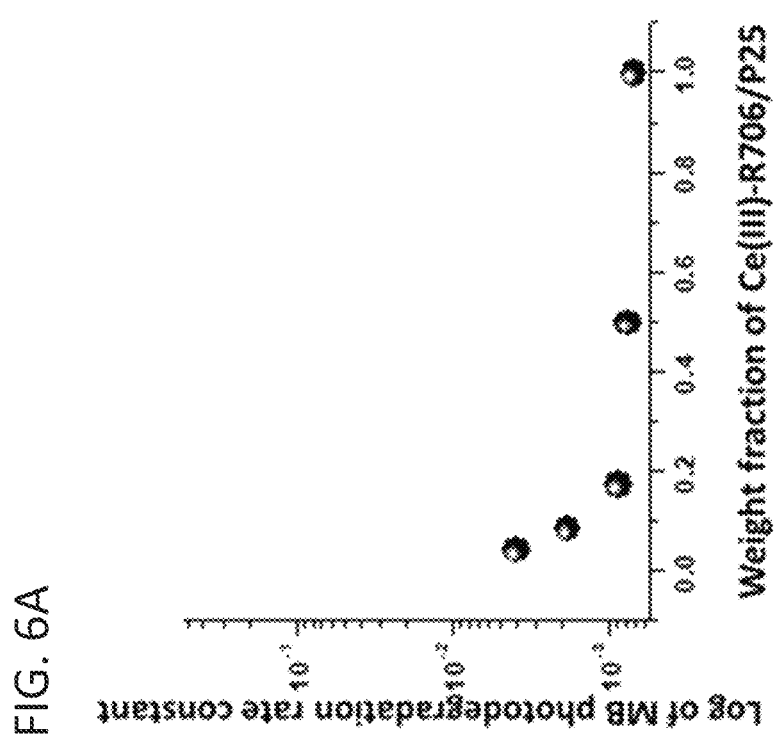

To understand what the minimum required amount of Ce (III)-R706 is in order to affect efficient inhibition of MB organic dye photodegradation, a series of photocatalysis reactions were conducted, in which the amount of Ce (III)-R706 was varied, while the amount of P25 in the aqueous dispersion was held fixed. Results of this experiment are presented in FIG. 6A, in terms of the rate constant for MB organic dye photodegradation as affected by the ratio of surface area of Ce (III)-R706 to that of the P25 photocatalyst. FIG. 6A is a plot of the photodegradation rate constant of $10^{-5}$ M MB organic dye degradation versus the weight fraction of Ce (III)-R706 relative to the P25. This data demonstrates that when this molar ratio is 0.2 or higher, there is highly effective inhibition of MB organic dye photodegradation.

The effect of the cerium valence states was also investigated in terms of having pure cerium (III) versus an equimolar mixture of cerium (III) and cerium (IV) valence states, within the cerium compound affecting photopassivation. For this comparison, a new material, Ce (III)/Ce (IV)-R706 was obtained by the precipitation of cerium on the surface of Ti-Pure R706 from an equimolar mixture of cerium (III) and cerium (IV) salts. Ce (III)/Ce (IV)-R706 was thus synthesized in a similar fashion to Ce (III)-R706 (obtained in Example 2), except for the following change: (i) in Step A of the synthesis, 0.52 g of ammonium cerium (III) nitrate tetrahydrate and 0.495 g of ammonium cerium (IV) nitrate (equimolar amount of cerium (III) and cerium (IV) in solution) were dissolved in 18 mL of water.

The effectiveness of Ce (III)/Ce (IV)-R706 as a photopassivant was assessed in a similar manner to Ce (III)-R706 in the paragraph above, by varying the relative amount of Ce (III)/Ce (IV)-R706 and conducting photocatalysis in a 10 mL dispersion of $10^{-5}$ M MB organic dye comprising a fixed amount of P25 photocatalyst. The results are shown in FIG. 6B. FIG. 6B is a plot of the photodegradation rate constant of $10^{-5}$ M MB organic dye degradation versus the weight fraction of Ce(III)/Ce(IV-R706) relative to the P25.

As can be seen, the rate constant for MB organic dye photodegradation is significantly higher at the same value on the x-axis when using Ce (III)/Ce (IV)-R706 compared to Ce (III)-R706. Even at a maximum investigated weight fraction of unity, the rate constant for MB organic dye photodegradation is nearly a factor of ten lower for Ce (III)-R706 in the FIG. 6A as compared with the Ce (III)/Ce (IV)-R706 passivant in FIG. 6B. Thus, the data clearly shows the advantage of using a pure cerium (III) compound instead of a mixed valence compound that consists of both cerium (III) and cerium (IV) valence states, in the material used for inhibiting photodegradation or organics.

Photostabilization of Organic Dye in a Solid (Dried) Composition Comprising Photocatalyst and Ce (III)-R706:

The examples above pertain to decreasing photodegradation of organic dye in the wet (liquid) state. The example that follows demonstrates that a similar approach can be used to achieve efficient photopassivation of a photocatalyst in the dry (solid) film state.

To investigate the effectiveness of this approach in a dry (solid) composition, Congo Red (CR) organic dye at a concentration of $3 \times 10^{-5}$ M was incorporated into a waterborne acrylic paint formulation dispersion, together with P25 photocatalyst (10 wt % relative to the Ti-Pure R706 pigment weight used in the dispersion).

A composition was made with 16% Ce (III)-R706 pigment volume concentration comprising CR organic dye (the pigment volume concentration is defined as the volume percentage of solid particles in the system after formation of the composition (e.g., excluding water). This was performed by first preparing a 75 wt % aqueous slurry of Ce (III)-R706 pigment by high shear mixing in presence of 0.3 wt % TAMOL™ 1124 with respect to the weight of pigment. 4.64 g of this slurry was incorporated in 12.78 g of acrylic-based BP 8164 polymer (obtained from the Dow Chemical Company), to which was added 1.966 mL of $3.5 \times 10^{-4}$ M CR aqueous dye solution, and 10 wt % P25 photocatalyst (with respect to pigment weight). The resulting dispersion was mixed under high-shear conditions in a high speed mixer.

Thereafter, 0.6 g of 2020E thickener (a non-ionic urethane rheology modifier) was added into the slurry, and the resulting dispersion was mixed under high-shear conditions in a high-speed mixer, to obtain the final formulation dispersion. The solid (dried) film coating was prepared with a 3 mil (1 mil=0.001 inch) bar applicator on a polyacrylic substrate and dried for 48 h prior to conducting the photocatalysis experiments. During photocatalysis, all the coatings were exposed to sunlight (under similar conditions) for an exposure period of 6 hours. Prior to sunlight exposure, 100 mg of the coating was scraped off with a sharp blade, and was extracted in 1.5 mL of absolute ethanol for UV-visible spectroscopy analysis, to obtain a datum of CR organic dye concentration in the film prior to photocatalysis. Similarly, another 100 mg portion of coating scraped off and extracted after 6 hours of sunlight exposure, and the percentage of dye degradation was calculated by UV-visible spectrophotometry. As a control experiment, negligible CR organic dye photodegradation was observed in a formulation dispersion that lacked P25 (this control formulation dispersion was synthesized in the same way as above, except in the absence of P25), upon exposure of this control to sunlight for a period of 6 h.

Figure 7B:
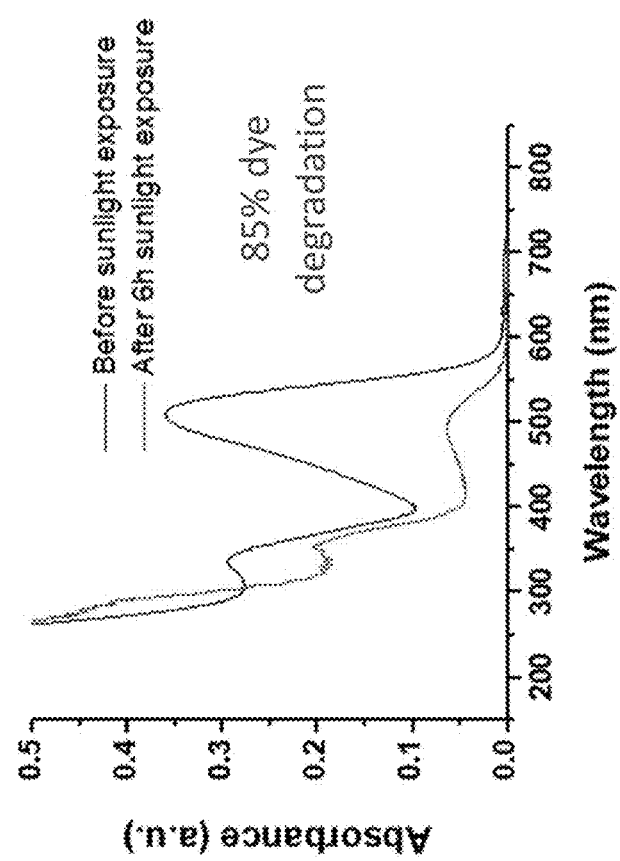
FIGS. 7A-7B are UV-visible spectra of congo red (CR) dye degradation before and after 6 h sunlight exposure in coating prepared with: 10% P25 and 90% Ce(III)-R706 (FIG. 7A) and 10% P25 and 90% unmodified Ti-Pure R706 (FIG. 7B).
Figure 7A:
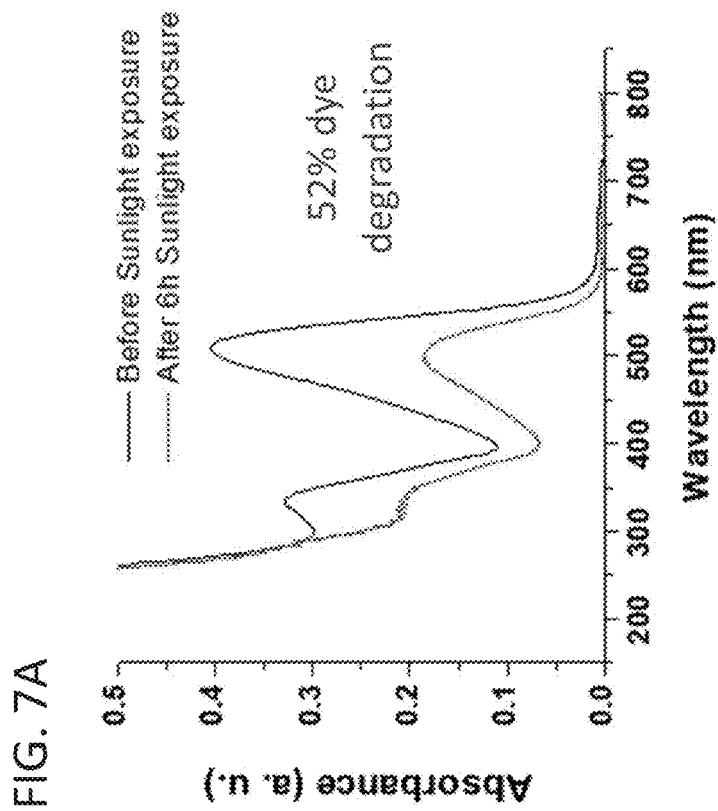

For the dispersion formulation comprising Ce (III)-R706 and P25 (90%: 10% w/w), FIG. 7A shows 52% CR organic dye degradation in the dried paint film, after exposure of this film to 6 h sunlight. FIG. 7A is a plot of absorbance versus wavelength obtained from UV-visible spectra of CR dye degradation before and after 6 h sunlight exposure in coating prepared with 10% photocatalyst P25 and 90% Ce (III)-R706.

FIG. 7B is a plot of absorbance versus wavelength obtained from UV-visible spectra of CR dye degradation before and after 6 h sunlight exposure in coating prepared with 10% photocatalyst P25 and 90% unmodified Ti-pure-R706. From FIG. 7B, it may be seen that the amount of CR organic dye degradation was 85% when using the comparative dispersion formulation comprising unmodified Ti-Pure R706 and P25 (90%: 10% w/w), after the same exposure to sunlight. These results demonstrate a higher inhibition efficiency of photodegradation of the organic dye in dried paint film when using Ce (III)-R706 compared with unmodified R706, in the presence of P25.

The experiment above demonstrates that Ce (III)-R706 inhibits the photodegradation of organics by an action-at-a-distance mechanism in the solid state. Similar results can also be obtained by preparing the equivalent of Ce (III)-R706 with another pigment, such as the rutile $TiO_2$ used in Example 1 (see FIG. 3), or another low-grade $TiO_2$—a class of pigment materials that are often used in paint compositions.

Example 3

This example was conducted to demonstrate photostabilization of organic dyes using a separate phase of cerium (III) carbonate.

Figure 8:
FIG. 8 is a photograph of white cerium (III) carbonate powder.

Synthesis and Characterization:

To a plastic vial, 1.04 g of solid ammonium carbonate was added and was mixed with 5 mL deionized water, to obtain a clear solution. Separately, 2 g of ammonium cerium (III) nitrate tetrahydrate were added to 20 mL of DI water, and were vortexed for 30 s to obtain a transparent solution. Thereafter, the aqueous solution containing the cerium (III) salt was added to the aqueous ammonium carbonate solution under vigorous stirring, resulting in a mixture of pH 9.1±0.1. To ensure a white Ce (III) carbonate product, it is required to achieve a sufficiently rapid mixing time upon the addition of the Ce (III) salt containing aqueous solution to the ammonium carbonate solution. This mixing time may be less than 4 minutes, less than 1 minute, less than 20 seconds, or less than 15 seconds. The mixture was subsequently stirred for 1 h, and was subsequently centrifuged at 15000 rpm for 3 min at 15° C. The white product obtained was washed with 100 mL of water by vortexing the aqueous slurry for 5 min followed by 5 min of sonication, before recovering the solids via centrifugation. This washing step was repeated for 2 more times in order to ensure removal of all loosely held ammonia species prior to yielding a wet paste (after centrifugation) having a solid content of 24.5 wt %. A small portion of this wet paste was dried, and the powder obtained remains a brilliant white color as shown in the FIG. 8.

Figure 9:
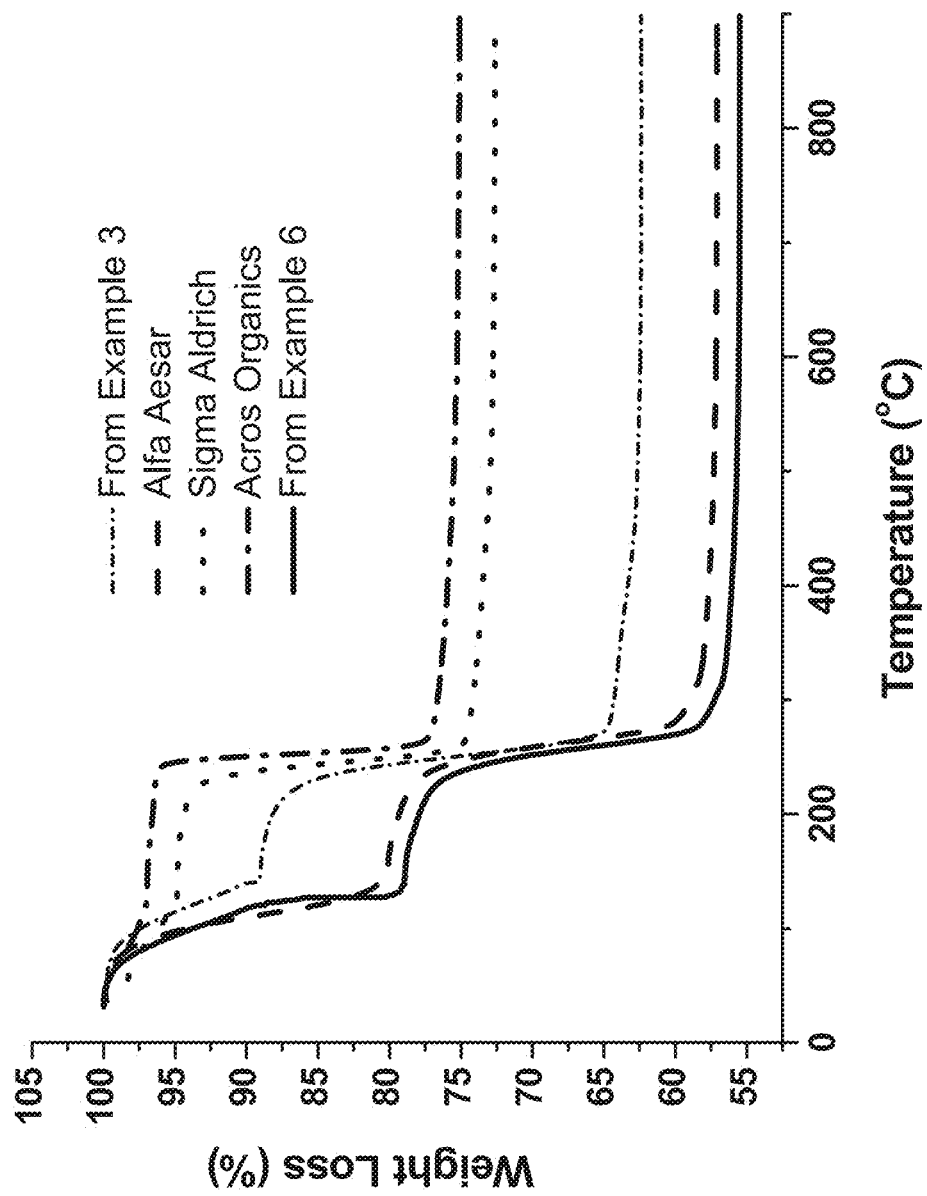
FIG. 9 is a TGA pattern of cerium(III) carbonate synthesized as described in Examples 3 and 6, along with several commercially available cerium(III) carbonate samples. All samples were dried at 80° C. for 16 hours prior to analysis.

The empirical formula of the white cerium (III) compound described above and shown in FIG. 8 is proposed on the basis of thermogravimetric analysis, a technique previously used by Liu et al (J. Cryst. Growth, 1999, 206, 88-92) and Zhai et al (Mater. Lett., 2007, 61, 1863-1866). FIG. 9 shows the TGA pattern of the white cerium (III) compound. This pattern shows an initial mass loss of about 11.9%, which corresponds to the loss of water, followed by a 25.7% mass loss, which corresponds to the loss of $CO_2$.

At 900° C., at the conclusion of the TGA experiment, 62.4% of the original mass is retained and corresponds to the presence of ceria ($CeO_2$). Thus, according to the TGA data in FIG. 9, the composition of the Ce dried precursor after synthesis is $Ce_2(CO_3)_3.4H_2O$. FIG. 9 is a graph of weight loss versus temperature conducted in a thermogravimetric analyser in dry air at a temperature ramp rate of 5° C./min for cerium (III) carbonate synthesized as described above and dried at 80° C. for 16 hours (h) prior to thermogravimetric analysis.

Powder X-ray diffraction (PXRD) analysis of the cerium (III) compound exhibits sharp lines that are consistent with the compound being highly crystalline. Transmission electron microscopy shows that the synthesis above leads to a range of particle sizes in the range varying from 5 μm to 10 μm in cross section, though one skilled in the art would recognize that tailoring the synthesis so as to yield smaller particles such as those that are on the length scale of 100 nm and smaller in cross section would be more preferred for a photopassivation application, which is generally more effective at a higher surface-to-volume ratio.

Photostabilization of MB Organic Dye in Solution Phase Using a Separate Phase of Cerium (III) Carbonate:

In all of the examples above, the insoluble cerium (III) compound that serves as a photopassivant has been in the form of being precipitated proximate to the surface of inorganic-oxide pigment particles (e.g., rutile $TiO_2$, Ti-Pure R706, silica, or the like).

In Example 3 it was investigated whether it is possible to incorporate a cerium (III) compound as an effective photopassivant as a separate phase.

The action-at-a-distance mechanism (observed in many of the examples above, in which efficient quenching of photocatalysis was achieved even with the cerium (III) compound not in contact with the photocatalyst surface) prompted this investigation. For example, consider data in the FIG. 6A, which showed that a reduced rate constant (on the order of $7.2 \times 10^{-4}$ min$^{-1}$) for photodegradation of MB organic dye could be achieved by adding an equivalent surface area of Ce (III)-R706 relative to P25. Thus, 11.4 mg of Ce (III)-R706 and 2 mg of P25 were used for the photocatalytic reaction of MB organic dye. Elemental quantification of Ce (III)-R706 from neutron activation analysis showed that Ce (III)-R706 consists of 4.4 wt % of Ce relative to the weight of R706. This means that 11.4 mg of Ce (III)-R706 (the amount used for the photocatalysis of MB organic dye) contains 0.5 mg of Ce in Ce (III)-R706. An attempt was therefore made to address the following question related to this example: Is it possible to add the cerium (III) compound as 0.5 mg of Ce in a cerium (III) carbonate phase, without precipitating it proximate to the surface of Ti-Pure R-706 to synthesize Ce (III)-R706, and still achieve comparable photopassivation, via an action-at-a-distance mechanism?

Figure 10:
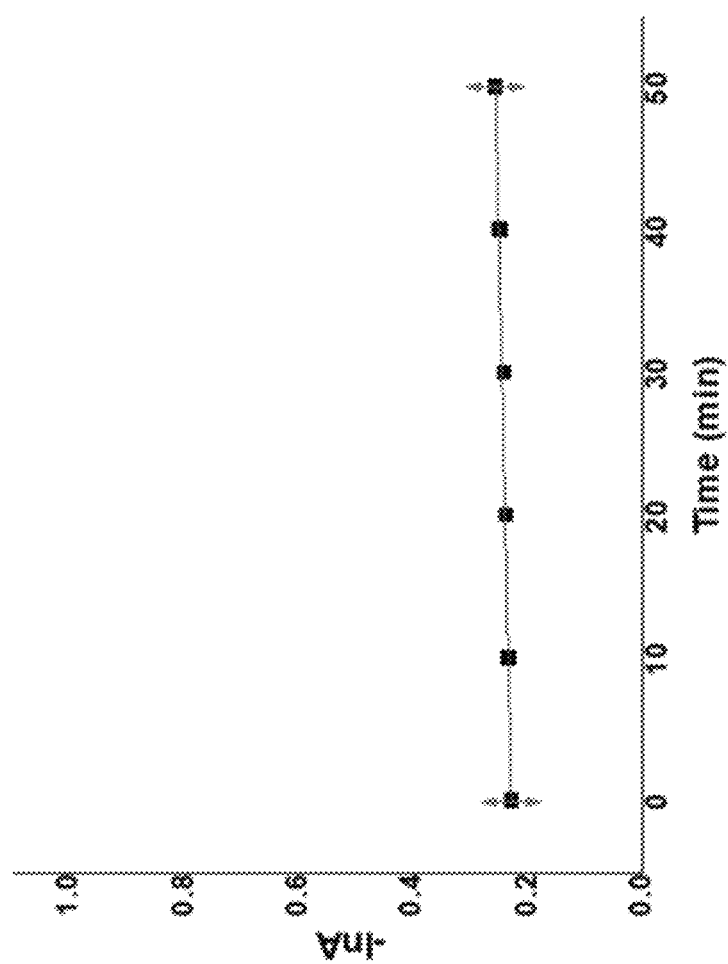
FIG. 10 is a plot of kinetics of $10^{-5}$ M MB organic dye degradation (under 254 nm light) in presence of 2 mg of P25, 11.4 mg of unmodified R706 and separately added 1 mg of $Ce_2(CO_3)_3 \cdot 4H_2O$.

1.0 mg of $Ce_2(CO_3)_3.4H_2O$ particles (which is equivalent to 0.5 mg of Ce) as its own phase were incorporated into a $10^{-5}$ M MB organic dye aqueous slurry containing 2 mg of P25 and 11.4 mg of Ti-Pure R706. FIG. 10 is a plot of −lnA versus time for $10^{-5}$ M MB organic dye degradation (under 254 nm light) in presence of 2 mg of P25, 11.4 mg of unmodified Ti-pure R706 and separately added 1 mg of $Ce_2(CO_3)_3.4H_2O$.

The rate constant calculated from the data in the FIG. 10 is $5.5 \times 10^{-4}$ min$^{-1}$, which is 1.5-fold lower than that achieved with the same amount of cerium, when using Ce (III)-R706, in the FIG. 6A of Example 2. Based on the results above, it is surmised that the incorporation of externally prepared insoluble $Ce_2(CO_3)_3.4H_2O$ particles is preferred for the inhibition of photodegradation of organic molecules than its precipitation proximate to an existing support surface of a separate phase, such as Ti-Pure R706.

Photostabilization of CR Organic Dye in a Solid (Dried) Film Comprising R706 and a Separate Phase of Cerium (III) Carbonate:

To investigate the photopassivation effectiveness of a separate cerium (III) compound in a dry (solid) paint film coating, insoluble cerium (III) carbonate particles and CR organic dye at a concentration of $3 \times 10^{-5}$ M were incorporated into a waterborne acrylic paint formulation dispersion, using either Ti-Pure-R706 or the same rutile $TiO_2$ used in Example 1 as the pigment, and assessed the rate of dye photodegradation relative to an identical dispersion, in the absence of cerium (III) carbonate particles.

The composition of this dispersion, and the procedure for synthesizing the dried coating film is described in the paragraph below. The dispersion consists of a waterborne acrylic paint, which was formulated with 16% pigment volume concentration, using either unmodified Ti-Pure R706 or rutile $TiO_2$ as pigment. This was accomplished by first adding the desired amount of cerium (III) carbonate, corresponding to either 2 wt % or 5 wt % with respect to the weight of the pigment, to an aqueous solution comprising 1.966 mL of $3.5 \times 10^{-4}$ M CR aqueous dye solution and 12.78 g of acrylic-based BP 8164 polymer (product of Dow Chemical). Separately, a 75 wt % aqueous slurry of either Ti-Pure-R706 or rutile $TiO_2$ was prepared by high shear mixing in the presence of 0.3 wt % of TAMOL™ 1124 with respect to the pigment weight. 4.64 g of this latter slurry (actual weight of pigment is 3.5 g) was incorporated into the above acrylic polymer-containing slurry, and the resulting dispersion was mixed under high-shear conditions in a high-speed mixer.

Finally, 0.6 g of 2020E thickener was added to the slurry, and the resulting dispersion was mixed under high-shear conditions in a speed mixer, to obtain the composition. The solid (dried) film coating was prepared with a 3 mil bar applicator on a polyacrylic substrate, and dried for 48 h prior to conducting photocatalysis experiments. During photocatalysis, all of the coatings were exposed to sunlight in a similar condition, for an exposure period of 6 h. Prior to sunlight exposure, 100 mg of the coating was scraped off with a sharp blade, and was extracted in 1.5 mL of absolute ethanol for UV-visible spectroscopic analysis, as a datum of CR organic dye concentration in the film prior to photocatalysis. Similarly, another 100 mg portion of coating was scraped off and extracted after 6 h of sunlight exposure, and the percentage of dye degradation was calculated by UV-visible spectrophotometry in comparison to the before photocatalysis sample.

Figure 11A:
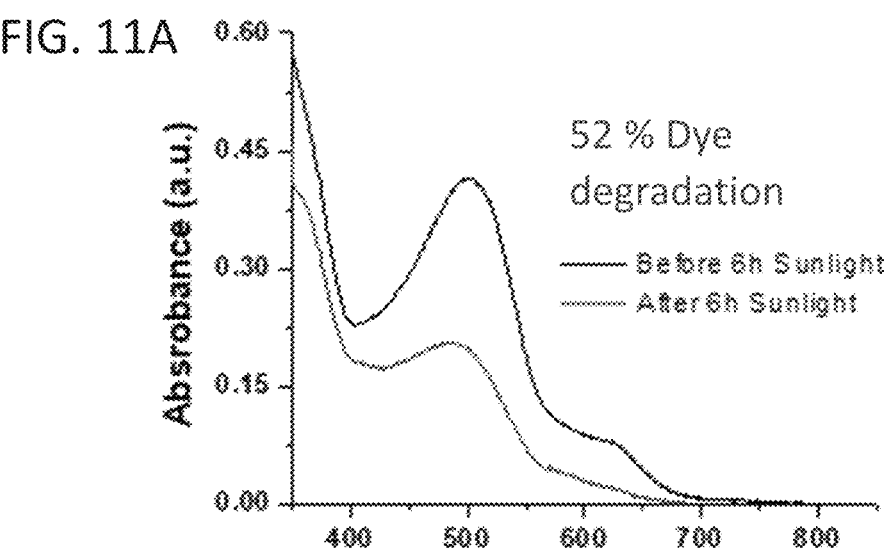
FIGS. 11A-11C are UV-visible spectra of CR organic dye before and after sunlight exposure in coating prepared with R706 and (i) 0 wt % Ce(III) carbonate (FIG. 11A); (ii) 2 wt % cerium(III) carbonate (FIG. 11C); and (iii) 5 wt % Ce(III)carbonate relative to R706 weight (FIG. 11C).
Figure 11B:
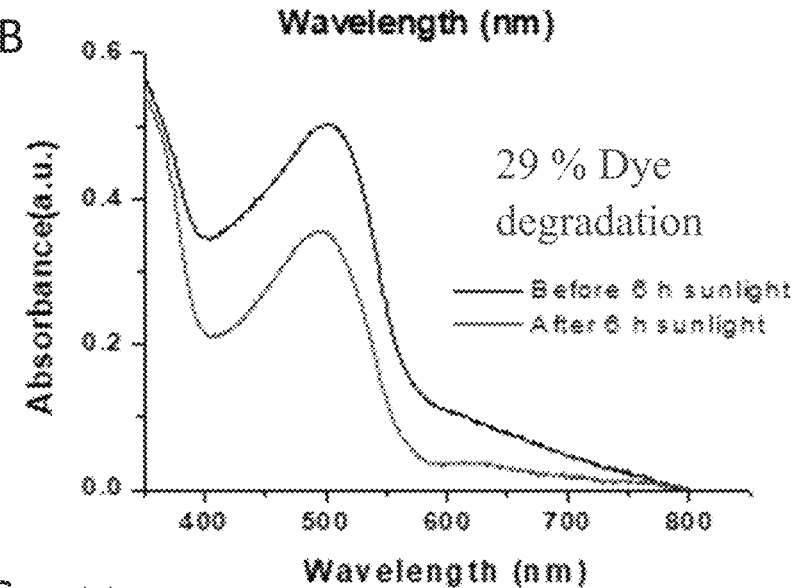
Figure 11C:
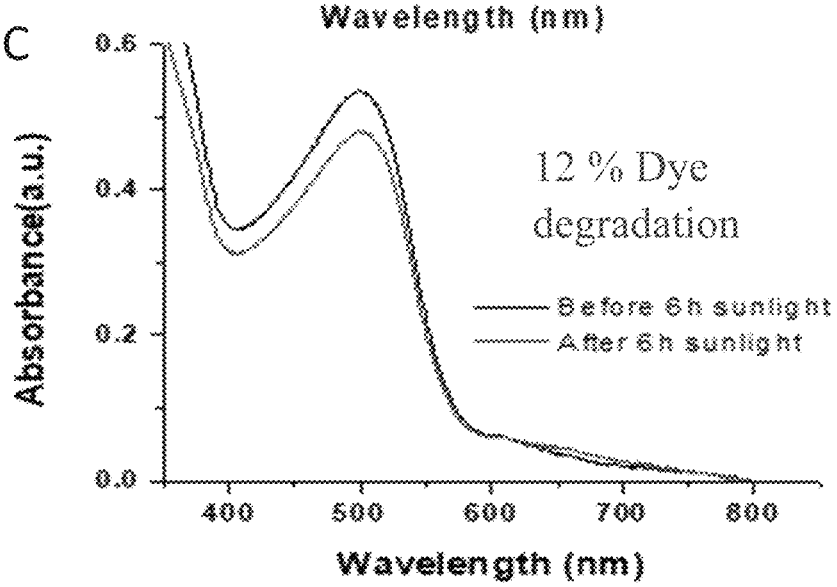

FIGS. 11A-11C show the extent of CR organic dye degradation in the dried paint film prepared with unmodified Ti-Pure-R706, when varying the amount of separately prepared cerium (III) carbonate, after exposure of films to 6 h of sunlight. It is clearly evident from the UV-visible spectra that with an increase in the wt. % of cerium (III) carbonate with respect to Ti-Pure R706 in the paint coating, the extent of photodegradation of CR organic dye decreased. In the absence of cerium (III) carbonate, FIG. 11A shows 52% photodegradation of the CR organic dye by R706 as photocatalyst. FIG. 11B shows that the percentage of photodegradation of CR organic dye decreased to 29% in the presence of 2 wt. % cerium (III) carbonate with respect to the weight of Ti-Pure R706 pigment (i.e. 70 mg of $Ce_2(CO_3)_3.4H_2O$ for 3.5 g of pigment). FIG. 11C shows that the percentage of photodegradation of CR organic dye by Ti-Pure R706 could be further decreased to 12% in the presence of 5 wt. % cerium (III) carbonate with respect to the weight of Ti-pure-R706 (i.e. 175 mg of $Ce_2(CO_3)_3.4H_2O$ for 3.5 g of pigment).

This data clearly demonstrates the photopassivation capability of a separate phase of insoluble cerium (III) compound, in a dry film containing only Ti-Pure R-706 as photocatalyst.

Figure 12A:
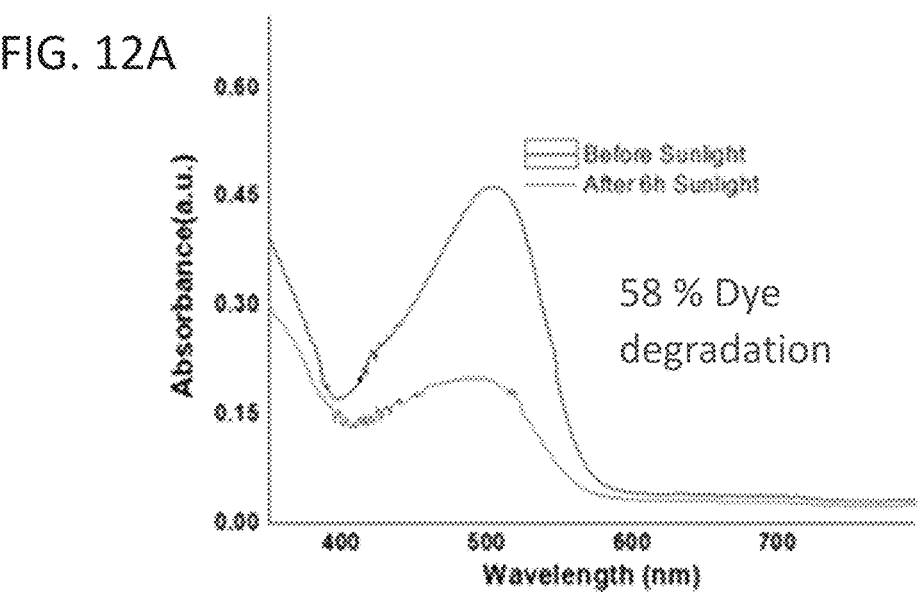
FIGS. 12A-12C are UV-visible spectra of CR dye before and after sunlight exposure in coating prepared with rutile $TiO_2$ and (i) 0 wt % Ce(III) carbonate (FIG. 12A); (ii) 2 wt % Ce(III) carbonate (FIG. 12B); and (iii) 5 wt % Ce(III) carbonate relative to $TiO_2$ weight (FIG. 12C).
Figure 12B:
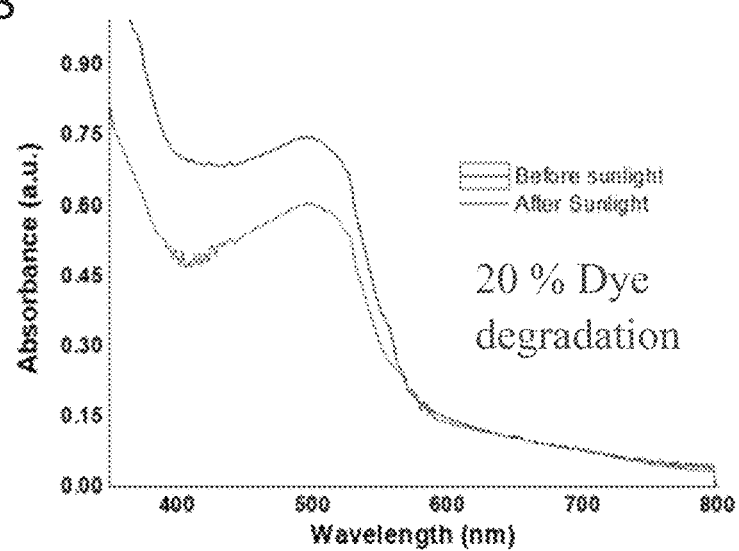
Figure 12C:
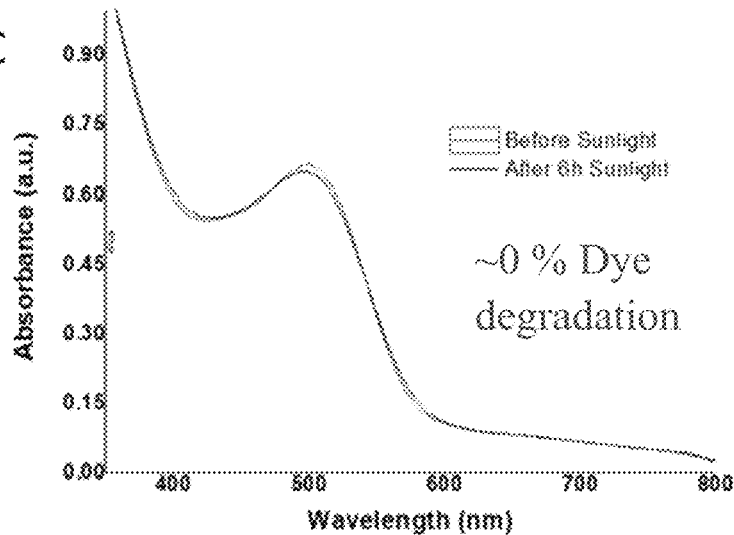

The photopassivation capability of the same insoluble cerium (III) carbonate as a separate phase was investigated in conjunction with the rutile $TiO_2$ used in Example 1 above, which was used as the pigment instead of Ti-Pure R-706 (as in the paragraph above). FIG. 12A shows that in coatings prepared without cerium (III) compound, photocatalysis by rutile $TiO_2$ caused a 58% photodegradation of CR organic dye after exposing the dry film to 6 h of sunlight (the control in Example 2 comprising only polymer and CR organic dye demonstrated no significant photodegradation of the dye in the absence of pigment). Data in FIG. 12B shows that the extent of dye degradation decreased to 20% when the coating was prepared with 2 wt % of cerium (III) carbonate with respect to weight of rutile $TiO_2$ pigment photocatalyst. Surprisingly, data in FIG. 12C shows that a coating prepared with 5 wt % cerium (III) carbonate together with rutile $TiO_2$ did not show any detectable CR dye photodegradation upon 6 h exposure in sunlight. This last data set demonstrates that a cheap grade of commercial $TiO_2$ can be successfully photopassivated via the action-at-a-distance mechanism of this invention, employing insoluble particles of cerium (III) carbonate as a separate cerium (III)-compound phase.

Example 4

Until now, in all of the examples above, Ce-based materials discussed for photopassivation of organic compounds have been synthesized by the inventors synthesis protocol (i.e. the synthesis of cerium carbonate given in Example 3). Here the inventors evaluated the photopassivation efficiency of commercially available Ce(III) carbonate hydrate, which were obtained from different chemical suppliers including Sigma Aldrich (325503-50G 99.9% trace metal basis); ACROS organics (AC379400500); and Alfa Aesar (15295-22).

Three separate sets of photocatalysis were performed via identical conditions and procedures as described in Example 3 (i.e. 10 mL of $10^{-5}$ M aqueous solution of methylene blue (MB) was treated with 2 mg of P25 photocatalyst, 11.4 mg of R706 and 1 mg of $Ce_2(CO_3)_3.xH_2O$ obtained from different commercial sources (i.e. Alfa Aesar, Sigma Aldrich and ACROS organics) in the same photoreactor setup). Surprisingly, $Ce_2(CO_3)_3.xH_2O$ obtained from Sigma-Aldrich and ACROS organics failed to exhibit photopassivation of MB dye, and within 30 sec~100% MB dye was degraded in aqueous solution under the exposure of 254 nm light in the photoreactor. However, $Ce_2(CO_3)_3.xH_2O$ obtained from Alfa Aesar showed efficient photopassivation of MB dye in solution, using the procedure above. FIG. 13A shows the kinetics of MB organic dye photodegradation from this experiment. The rate constant calculated from the data in FIG. 13A is $1 \times 10^{-3}$ $min^{-1}$, which is still ~2-fold faster MB degradation than that achieved with the same amount of $Ce_2(CO_3)_3.xH_2O$ synthesized according to Example 3 (See FIG. 10). Although $Ce_2(CO_3)_3.xH_2O$ from Sigma-Aldrich and ACROS organics failed to show the photopassivation of MB dye using the procedure above, when increasing the amount of $Ce_2(CO_3)_3.xH_2O$ from 1 mg to 5 mg, a reasonable amount of photopassivation of MD dye was observed in both cases (e.g., for Sigma-Aldrich and ACROS samples of $Ce_2(CO_3)_3.xH_2O$). FIGS. 13B and 13C show the kinetics of MB organic dye photodegradation from these experiments, and the rate constants calculated from the data in FIGS. 13B and 13C are $4.7\times10^{-3}$ min$^{-1}$ and $4\times10^{-3}$ min$^{-1}$, respectively. These data show 8.5-fold and 7.5-fold higher MB degradation under exposure of 254 nm light, compared with that achieved with the same amount of $Ce_2(CO_3)_3 \cdot xH_2O$ synthesized according to Example 3 (see FIG. 10).

ATR-FTIR was undertaken to explore the different nature of carbonate in the various $Ce_2(CO_3)_3 \cdot xH_2O$ materials. A striking difference obtained in the ATR-FTIR spectra of $Ce_2(CO_3)_3 \cdot xH_2O$ obtained from Sigma-Aldrich and ACROS organics is that both materials posses an intense peak at 1410 cm$^{-1}$ corresponding to weakly electrostatically attached carbonate, which is similar to the FTIR of free carbonate ion dissolved in water (Geochimica et Cosmochimica Acta, 2005, 69, 1527-1542). Although $Ce_2(CO_3)_3 \cdot xH_2O$ obtained from Alfa Aesar also exhibited a band at 1410 cm$^{-1}$, it was very weak in terms of intensity relative to other bands above e.g. band for unidentate carbonate. Surprisingly, the band at 1410 cm$^{-1}$ was entirely absent in the $Ce_2(CO_3)_3 \cdot xH_2O$ synthesized according to Example 3. The inventors utilized the ratio of peak intensity at 1410 cm$^{-1}$ (electrostatically attached carbonate) to peak at 1468 cm$^{-1}$ (monodentate carbonate) as a measure of presence of electrostatically attached carbonate in the $Ce_2(CO_3)_3 \cdot xH_2O$, and values are tabulated in Table 1, based on spectra shown in FIG. 14. Based on data, $Ce_2(CO_3)_3 \cdot xH_2O$ possessing a ratio of peak intensity at or below 0.93 is preferable for photopassivation of organics at 1 mg scale in presence of 2 mg P25. But zero peak ratio is most preferable i.e. absence of band at 1410 cm$^{-1}$. When $Ce_2(CO_3)_3 \cdot xH_2O$ has weakly electrostatically attached carbonate as evidenced by appreciable 1410 cm$^{-1}$ band intensity in the infrared, the cerium carbonate has reduced photopassivation ability.

TABLE 1

| Sample Name | Ratio of ATR-FTIR peak intensity 1410 cm$^{-1}$:1468 cm$^{-1}$ |
| --- | --- |
| Synthesized According to Example 3 | 0.00 (no band) |
| Alfa- Aesar | 0.9 |
| Sigma Aldrich | 1.3 |
| ACROS organic | 1.3 |

To further investigate differences in photopasssivation ability of commercial $Ce_2(CO_3)_3 \cdot xH_2O$ and $Ce_2(CO_3)_3 \cdot 4H_2O$ synthesized according to Example 3, CHN elemental analysis was performed. It was found that $Ce_2(CO_3)_3 \cdot xH_2O$ obtained from Sigma-Aldrich and ACROS organics contained 5.71% C and 0.93% H and 5.74% C and 0.88% H, respectively, whereas $Ce_2(CO_3)_3 \cdot xH_2O$ obtained from Alfa Aesar contained 6.5% C and 1.45% H. The $Ce_2(CO_3)_3 \cdot 4H_2O$ synthesized according to Example 3 contained 6.7% C and 1.76% H. Based on this data, it is preferred for cerium carbonate to have both a high C and H amount. It is less preferred to have cerium carbonate comprising a weight % C of 5.7% or lower, while comprising a weight % H of 0.9% or lower. Alternatively, it is more preferred for the cerium carbonate to have weight % C of 6.5% or higher and H weight % of 1.5% or higher.

A further tool to characterize and differentiate different batches of cerium carbonate pertaining to this invention is thermogravimetric analysis. This analysis relies on the thermal decomposition of cerium carbonate to synthesize cerium oxide and $CO_2$, which occurs in the temperature range of 200° C. to 575° C. (see J. Cryst. Growth 1999, 206, 88-92 and Mater. Lett. 2007, 61, 1863-1866). Data in FIG. 9 and Table 2 summarizes the percentage weight loss in the temperature range of 200° C. to 575° C., as normalized relative to the dehydrated weight at 200° C., during thermogravimetric analysis of various cerium carbonate batches in dry air at a heating ramp rate of 5° C./min. The cerium (III) carbonate synthesized according to Example 3 has the largest weight loss corresponding to $CO_2$ released normalized to the dehydrated weight at 200° C. of 29.0% (difference in weight between 200° C. and 575° C., divided by the dry weight at 200° C.), whereas the batches of cerium (III) carbonate received from Sigma Aldrich and Acros Organics have the lowest weight loss of 22.7% and 21.9%, respectively.

TABLE 2

| Sample Name | Weight loss in the range of 200° C. to 575° C. corresponding to $CO_2$ released (wt % normalized to dehydrated weight at 200° C.) |
| --- | --- |
| ACROS organics | 21.9% |
| Sigma Aldrich | 22.7% |
| Alfa Aesar | 27.5% |
| Synthesized According to Example 3 | 29.0% |

Based on these data in FIG. 9 and Table 2, it can be concluded that the most preferable cerium carbonate has a weight loss corresponding to $CO_2$ released during thermogravimetric analysis of at least 29.0% as normalized to the dry weight of the material. A more preferable batch of cerium carbonate of this invention has a weight loss corresponding to $CO_2$ released during thermogravimetric analysis of at least 27.6% as normalized to the dry weight of the material. A preferable batch of cerium carbonate of this invention a weight loss corresponding to $CO_2$ released during thermogravimetric analysis of at least 21.9% as normalized to the dry weight of the material.

Based on the above data, all of the commercial $Ce_2(CO_3)_3 \cdot xH_2O$ are capable to do photopassivation of organic molecules via an action-at-a-distance mechanism, however, either due to presence of less carbonate or due to the presence of electrostatically attached carbonate, they are not as efficient as the inventors' $Ce_2(CO_3)_3 \cdot 4H_2O$ synthesized according to Example 3. Thus, higher amounts of commercial $Ce_2(CO_3)_3 \cdot xH_2O$ are required to scavenge the ROS generated by photocatalyst.

Example 5

Though photocatalysis increases photodecomposition of organics, thought to be mediated by generation of reactive oxygen species (ROS), organic molecules have their own absorptivity of light due to presence of light-absorbing chemical substituents. This absorptivity of light can itself produce radicals in water, which even in the absence of a photocatalyst per se, can ultimately lead to photodegradation/decomposition of organics. Here the inventors investigated whether it was possible to reduce the inherent photodecomposition/degradation of methylene blue (MB) dye under exposure to 254 nm light, by using cerium (III) carbonate, in the absence of any added photocatalyst.

Two separate sets of photoreactions were performed: (1) 10 mL aqueous solution of 10$^{-5}$ M MB dye was exposed to 254 nm light under a photoreactor setup for a duration of up to 60 min and (2) 1 mg $Ce_2(CO_3)_3 \cdot 4H_2O$ that was synthesized according to the procedure described in Example 3 was dispersed in a 10 mL aqueous solution of $10^{-5}$ M MB dye, and the resulting slurry was exposed to 254 nm light under photoreactor setup for a duration of up to 60 min. Data shown in FIGS. 15A-15B demonstrate that the aqueous solution of $10^{-5}$ M methylene blue containing 1 mg $Ce_2(CO_3)_3 \cdot 4H_2O$ exhibited a nearly 40-fold decreased rate of MB dye photodecomposition compared to the control aqueous solution consisting of $10^{-5}$ M MB dye.

Example 6

Synthesis of Cerium(III) Carbonate via Solid-State Mechanochemical Method and its Use in the Photostabilization of an Organic Dye
Synthesis and Characterization of Cerium(III) Carbonate:

To a mortar, 1.04 g of solid ammonium carbonate and 2 g of ammonium cerium (III) nitrate tetrahydrate were added and ground with a pestle for 5 min. The resulting white powder was washed with water (including 5 min vortexing and 5 min sonication), and the solid product was recovered via centrifugation at 20000 rpm for 3 min. The solid product obtained was further washed three more times, in order to ensure the removal of any unreacted or loosely held salt species prior to yielding a wet paste after centrifugation having a solid content of 24.5 wt. %. A small portion of this wet paste was dried, to obtain a white colored powder.

Powder XRD of the mechanochemically synthesized Ce(III) carbonate demonstrated a pattern consistent with a crystalline material with the known crystal structure of $Ce_2(CO_3)_3 \cdot 6H_2O$. As in Example 4, ATR-FTIR was undertaken to explore the nature of carbonate in $Ce_2(CO_3)_3 \cdot 6H_2O$, and the ATR-FTIR spectrum exhibited the absence of a weakly electrostatically attached carbonate band at 1410 $cm^{-1}$ in FIG. 14, similar to the wet chemically synthesized $Ce_2(CO_3)_3 \cdot 4H_2O$ of Example 3. Thermogravimetric analysis in dry air at a heating ramp rate of 5° C./min demonstrated 28.4 wt % $CO_2$ was released (difference in weight between 200° C. and 575° C., divided by the dry weight at 200° C.), and this data is shown in FIG. 9.

Photocatalysis was performed via identical conditions and procedures as described in Example 3 (i.e. 10 mL of $10^{-5}$ M aqueous solution of methylene blue (MB) was treated with 2 mg of P25 photocatalyst, 11.4 mg of R706 and 1 mg of $Ce_2(CO_3)_3 \cdot 6H_2O$ in the same photoreactor setup). FIG. 16 shows the kinetics of MB organic dye photodegradation from this experiment. The rate constant calculated from the data in FIG. 16 is $6 \times 10^{-4}$ $min^{-1}$, which is very similar to the rate constant obtained for $Ce_2(CO_3)_3 \cdot 4H_2O$ (i.e. $5.5 \times 10^{-4}$ $min^{-1}$) of Example 3.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

While various embodiments and aspects are shown and described herein, it will be obvious to those skilled in the art that such embodiments and aspects are provided by way of example only. Numerous variations, changes, and substitutions will now occur to those skilled in the art. It should be understood that various alternatives to the embodiments described herein may be employed.

The invention claimed is:

1. A composition comprising distinct particles of cerium (III) carbonate and a pigment selected from the group consisting of zinc oxide, calcium carbonate, mica, silicas, talcs, barium sulfate, clays, and calcined clays.

2. The composition of claim 1, wherein the pigment is zinc oxide.

3. The composition of claim 1, wherein the pigment is calcium carbonate.

4. The composition of claim 1, wherein the pigment is mica.

5. The composition of claim 1, wherein the pigment is a silica.

6. The composition of claim 1, wherein the pigment is a talc.

7. The composition of claim 1, wherein the pigment is barium sulfate.

8. The composition of claim 1, wherein the pigment is a clay or a calcined clay.

9. A composition comprising distinct particles of cerium (III) carbonate; and a pigment or a dye or a combination thereof, wherein the pigment is selected from the group consisting of titanium dioxide, zinc oxide, zirconium oxide, tungsten oxide, vanadium oxide, tin oxide, nickel oxide, copper oxide, molybdenum oxide, tungsten sulfide, cadmium sulfide, cadmium selenide, zinc sulfide, calcium carbonate, mica, silicas, talcs, graphite, white lead, barium sulfate, lithopone, clays, calcined clays lead silico-chromate, zinc chromate, calcium zinc molybdate, and barium metaborate.

10. The composition of claim 9, wherein the composition comprises a pigment which is titanium dioxide.

11. The composition of claim 9, which comprises a dye selected from the group consisting of: iron oxide, carbon black, cadmium sulfide, toluidene red, chrome orange, chrome yellow, chrome green, polyazaindacenes, coumarins, lanthanide complexes, hydrocarbon and substituted hydrocarbon dyes, polycyclic aromatic hydrocarbons, scintillation dyes, aryl- and heteroaryl-substituted polyolefins, carbocyanine dyes, phthalocyanine dyes and pigments, oxazine dyes, carbostyryl dyes, porphyrin dyes, acridine dyes, anthraquinone dyes, anthrapyridone dyes, naphtalimide dyes, benzimidazole derivatives, arylmethane dyes, azo dyes, diazonium dyes, nitro dyes, quinone imine dyes, tetrazolium dyes, thiazole dyes, perylene dyes, perinone dyes, bis-benzoxazolylthiophene, xanthene dyes, indigoid dyes, chromones dyes, flavones dyes, thiazine dyes, and combinations thereof.

12. The composition of claim 9, which comprises a dye selected from the group consisting of: iron oxide, carbon black, cadmium sulfide, toluidene red, chrome orange, chrome yellow, chrome green, and combinations thereof.

13. The composition of claim 9, which comprises a dye which is methylene blue or congo red.

14. The composition of claim 9, wherein the cerium (III) carbonate releases at least 27.5 wt % $CO_2$ when normalized to the dry weight of the cerium (III) carbonate, during thermogravimetric analysis.

15. The composition of claim 9, wherein the cerium (III) carbonate is the cerium carbonate is $Ce_2(CO_3)_3 \cdot 4H_2O$ or $Ce_2(CO_3)_3 \cdot 6H_2O$.

* * * * *